(12) United States Patent
Katou

(10) Patent No.: US 8,585,700 B2
(45) Date of Patent: Nov. 19, 2013

(54) MEDICAL DEVICE

(75) Inventor: Yukitoshi Katou, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 938 days.

(21) Appl. No.: 12/713,870

(22) Filed: Feb. 26, 2010

(65) Prior Publication Data

US 2010/0152732 A1 Jun. 17, 2010

Related U.S. Application Data

(63) Continuation of application No. PCT/JP2008/065280, filed on Aug. 27, 2008.

(30) Foreign Application Priority Data

Aug. 28, 2007 (JP) .................................. 2007-221901
Mar. 26, 2008 (JP) .................................. 2008-081424

(51) Int. Cl.
*A61B 18/14* (2006.01)

(52) U.S. Cl.
USPC .............................. 606/49; 606/50; 606/215

(58) Field of Classification Search
USPC ............................................ 606/49–52, 215
See application file for complete search history.

(56) References Cited

U.S. PATENT DOCUMENTS

| | | | |
|---|---|---|---|
| 2002/0128644 A1* | 9/2002 | Hata et al. ...................... | 606/34 |
| 2002/0147447 A1* | 10/2002 | Long ............................... | 606/41 |
| 2002/0151890 A1* | 10/2002 | Scholer et al. .................. | 606/48 |
| 2004/0116949 A1* | 6/2004 | Ewers et al. ................... | 606/167 |
| 2004/0199160 A1* | 10/2004 | Slater .............................. | 606/48 |
| 2004/0230185 A1 | 11/2004 | Malecki et al. | |
| 2004/0243122 A1 | 12/2004 | Auth et al. | |
| 2004/0267257 A1* | 12/2004 | Bourne et al. .................. | 606/41 |
| 2005/0216039 A1* | 9/2005 | Lederman ..................... | 606/144 |
| 2006/0241582 A1 | 10/2006 | Malecki et al. | |
| 2006/0271030 A1 | 11/2006 | Francis et al. | |
| 2007/0106290 A1 | 5/2007 | Turano et al. | |
| 2007/0112347 A1 | 5/2007 | Malecki et al. | |
| 2009/0005780 A1* | 1/2009 | Kato .............................. | 606/50 |
| 2009/0069810 A1* | 3/2009 | Kuroda et al. .................. | 606/51 |

FOREIGN PATENT DOCUMENTS

| | | |
|---|---|---|
| JP | 59-177411 U | 11/1994 |
| JP | 2000-210301 A | 8/2000 |
| JP | 2006-521181 A | 9/2006 |
| WO | WO 2004/086944 A2 | 10/2004 |
| WO | WO 2006/110830 A2 | 10/2006 |
| WO | WO 2007/100067 A1 | 9/2007 |

OTHER PUBLICATIONS

International Search Report issued by the International Searching Authority (Japanese Patent Office) on Nov. 6, 2008 in International Application No. PCT/JP2008/065280.

* cited by examiner

*Primary Examiner* — Michael Peffley
*Assistant Examiner* — Khadijeh Vahdat
(74) *Attorney, Agent, or Firm* — Buchanan Ingersoll & Rooney PC

(57) ABSTRACT

A medical device is configured to perform a holding operation by a clamping mechanism with respect to a biological tissue at a periphery of a defect and a supply operation of electric energy independently by flowing current in the clamping mechanism while sandwiching biological tissue composed of an atrial septum secundum and a foramen ovale valve by way of the clamping mechanism to fuse the biological tissues by, for example, turning on a switch which on-off controls the supply of the electric energy.

19 Claims, 13 Drawing Sheets

MEDICAL DEVICE

This application is a continuation of International Application No. PCT/JP2008/065280 filed on Aug. 27, 2008, and claims priority to Japanese Application No. 2007-221901 filed on Aug. 28, 2007 and Japanese Application No. 2008-081424 filed on Mar. 26, 2008, the entire content of all three of which is incorporated herein by reference.

TECHNOLOGICAL FIELD

The disclosure here relates to a medical device. More specifically, the disclosure here pertains to a medical device used for medical treatment or the like to close a defect occurring in a living body.

BACKGROUND DISCUSSION

Recently, a device described in International Application Publication No. WO/2004/086944 has been proposed as a medical treatment device for a patent foramen ovale (hereinafter, referred to as PFO: Patent Foramen ovale) which is a cardiogenic factor of a stroke and a hemi headache.

This PFO closing device is a device in which an apparatus is inserted into the foramen ovale from the right atrium toward the left atrium, a foramen ovale valve is pulled to the foramen ovale to close it, and the biological tissue is fused by applying electric energy.

However, the foramen ovale, the foramen ovale valve and the atrial septum secundum are different not only with respect to size, but also with respect to a state of thickness, shape or the like. Depending on the person and according to other circumstances, the size or the like of the apparatus may be restricted a lot. Also, even on an occasion when the procedure is performed, there is a fear that it becomes difficult to pull various forms of foramen ovale valves to the foramen ovale in a desired and reliable manner.

Consequently, the applicant here previously proposed a PFO closing device in which the foramen ovale valve and the atrial septum secundum are sandwiched by a pair of electrodes, and the biological tissue is fused reliably by applying electric energy from both the electrodes. This PFO closing device is shown in International Application Publication No. WO/2007/100067.

This device uses clamping means in which one side thereof is made of a sticking member composed of a needle electrode and the other side thereof is made of a sandwiching member for sandwiching the foramen ovale valve and the atrial septum secundum with respect to the sticking member. The sticking member is stuck into the foramen ovale valve and thereafter, the foramen ovale valve and the atrial septum secundum are sandwiched with respect to the sandwich member which is the other electrode, electrical energy is applied to the biological tissue, and fusion is carried out.

This device can be used also in case of closing defects such as a congenital atrial septum secundum defect (ASD), a PFO, a ventricular septal defect (VSD) and a patent ductus arteriosus (PDA). It is also a device having high general versatility and in particular, foreign substances are not indwelled in the body, the constitution becomes simple, also the procedure becomes easy and the foramen ovale valve and the atrial septum secundum can be fused reliably.

However, to steer this device, a cable for supplying electric energy and a fine and long-line shaped member for steering the clamping means remotely are provided on the steering unit, so that various steering means exist in the steering unit and there is a fear of miss-steering. In particular, in case of sandwiching a tissue and thereafter fusing it by applying electric energy, when the electric energy is applied, there is a fear that electric current flows not only in the desired region but also in an unnecessary region. There is also a fear that a thrombus will be attached depending on the temperature-rise of the sticking member or the like. When the thrombus is exfoliated from the sticking member or the like and reaches a peripheral vessel of the brain from the left atrium, a cerebral infarction or the like would occur, so that the attachment of the thrombus should be prevented as much as possible.

Also, in case of sandwiching a biological tissue by clamping means, the surgery operator sticks a sticking member to the foramen ovale valve while maintaining a state in which the foramen ovale valve which has a thin-film shape and is easily deformed is held by a sandwiching member. Specifically, for example, in a state in which the sandwiching member is held by the left hand so as not to be displaced, the sticking member is steered by the right hand and the sticking is executed, but when the holding by the left hand is loosened, the sticking cannot be executed and therefore, there is also such a practical problem that the operator must concentrate on both the right and left hands.

SUMMARY

The medical device disclosed here is able to perform a sandwiching operation of biological tissue with a clamping mechanism and a supply operation of electric energy independently. This helps reliably inhibit or prevent a thrombus attachment caused by the temperature-rise of the sticking member or the like, which is caused by unnecessary electric current flow. Also, the construction of the steering or moving unit is simplified, and it is possible to perform a surgical procedure relatively smoothly, safely and reliably.

According to one aspect, a medical device comprises a catheter configured to be positioned in a blood vessel, a sticking member for sticking biological tissue at a periphery of a defect existing in a biological tissue, the sticking member being movably positioned in the catheter for movement in an advancing and retracting manner, a sandwiching member cooperating with the sticking member to sandwich the biological tissue between the sticking member and the sandwiching member to close the defect, the sandwiching member being movably positioned in the catheter for movement in an advancing and retracting manner, and two spaced apart contact members each connected to a conductive wire and connectable to an energy supply source that supplies energy to supply energy to the contact members. A movable sticking moving-member is connected to the sticking member to move the sticking member in the advancing and retracting manner, and a movable sandwiching moving-member is connected to the sandwiching member to move the sandwiching member in the advancing and retracting manner. A pair of terminals includes one terminal and an other terminal, the one terminal connected to one of the sandwiching moving-member and the sticking moving-member so the terminal moves together with the one of the sandwiching moving-member and the sticking moving-member during movement of the one of the sandwiching moving-member and the sticking moving-member, and the other terminal connected to the other of the sandwiching moving-member and the sticking moving-member. The sticking moving-member is movable to move the sticking member to stick the biological tissue, and the sandwiching moving-member is movable to move the sandwiching member to a position to cooperate with the sticking member in a sandwiching state in which the biological tissue is sandwiched between the sticking member and the sandwiching member to close the defect. The one terminal contacts one of the contact members in the sandwiching state and the other terminal contacts the other contact member so that with the conductive wire connected to the energy supply source, energy flows to the sticking member and the sandwiching member to fuse together the biological tissue sandwiched between the sandwiching member and the sticking member.

It is possible for the medical device here to supply electric energy after the sandwiching state of the biological tissue is established by the steering of the clamping means, so that it is possible to perform a surgical procedure relatively smoothly, safely and reliably. And it is possible to provide a medical device in which a thrombus attachment caused by temperature-rise along with the electric energy supply to an unnecessary region or at an unnecessary time point can be reliably inhibited or prevented.

A control unit for controlling the supply of energy can include a switch provided on the steering unit or in a vicinity thereof, or attachment and detachment. With this arrangement, it is possible for the electric energy supply to be carried out after biological tissue is sandwiched between a sticking member and a sandwiching member. In other words, if it is in a state in which the sticking member does not stick the biological tissue, the electric energy is not supplied, unnecessary electric energy supply does not occur, and the electric energy supply starts for the first time after the biological tissue is held and pressed, so that it is possible to inhibit or prevent miss-operation during the surgical procedure and to perform a surgical procedure relatively smoothly, safely and reliably, with quite good safety.

In a case in which the contact member and the terminal contact one another, and if the terminal and the contact member contact before reaching the moving completed position of the terminal, even if a sandwiching state of the sandwiching member changes depending on the sticking state of the sticking member (which may differ from person to person or depending on the differences in thickness of the atrial septum secundum), the electrical conduction becomes possible by adjusting the conducting position of the terminal or the contact member corresponding to this change.

The respective terminals contact the contact member along with the movement of the respective steering-members of the sticking member and the sandwiching member, so that the movement of the sticking member and the sandwiching member upon moving the respective level is linked with the electrical conductable state. An electrical conduction state does not arise unless a predetermined surgical procedure is completed and safety is secured also with respect to the sequence in the surgical procedure. However, as an alternative, either one of the groups of the contact members and the terminals which exist in pairs and which contact each other may be always in a contact state.

If the contact member is constituted by a tubular collar having an attachment portion, a leg portion and a spring, the associated terminal will contact the terminal before reaching the moving completed position. Therefore, with a relatively simple construction, it is possible to accommodate or address biological tissues which differ from person to person.

By providing respective steering-levers for the sticking member and for the sandwiching member, including levers which are slidably provided on the main body portion which is grippable by one hand, it is possible to perform the surgical procedure by the movement of the respective steering-levers and it is possible to attempt to realize relative smoothness, safety and reliability of the surgical procedure.

The sticking steering-lever can be configured to protrude to one surface of the flat main body portion of a housing, and the steering-lever for the sandwiching member can protrude to the other surface side, whereby miss-steering of the respective steering-levers is avoided, and it is possible to attempt to realize smoothness, safety and reliability of the surgical procedure.

By providing a main body portion on which the slide portion is mounted and configured to approach and separate with respect to the main body portion, if either one of sticking and sandwiching steering-levers is provided on the upper surface of the main body portion and if the other movement is carried out by the slide portion, one of the steering-levers lies on the upper surface of the main body portion and the other steering is to be carried out by the slide portion which is approached and separated with respect to the main body portion, and so it is possible to prevent miss-steering of the surgical procedure and to perform the surgical procedure smoothly, safely and reliably.

The medical device is preferably outfitted with a holding portion for holding the biological tissue non-retractably with respect to the sticking direction of the sticking member. The sticking or puncturing/penetration by the sticking member becomes relatively easy, and it is possible to accommodate various biological tissues which are all different depending on persons.

The medical device is also preferably provided with positioning hold means composed of a positioning portion for positioning the sticking member and a holding portion for holding the biological tissue non-retractably with respect to the sticking direction of aforesaid sticking member. This makes it possible, by the positioning portion, to position the sticking member relatively accurately with respect to the biological tissue having a defect, and the sticking of the sticking member becomes easier by the holding portion.

The positioning portion can be configured to displaces an elastic member outward by steering a long main operation rod advancingly and retractingly in the axis direction in a main tube provided advanceably and retractably in a catheter. If the elastic member positions the sticking member at a central portion of the defect by elastically attaching it at an inner edge of the defect of the biological tissue elastically, the positioning of the sticking member becomes possible only by moving the main operation rod advancingly and retractingly in the axis direction.

The holding portion can be constructed such that the distal portion of the main operation rod is curved and the biological tissue is held by steering or moving a long main operation rod advancingly and retractingly in the axis direction in a main tube provided advanceably and retractably in a catheter.

The long main operation rod is preferably rotatable by as much as 360 degrees centering around the center axis of the main tube. It is thus possible to insert the distal end of the device through the defect of the biological tissue easily regardless of the state of the biological tissue and it is possible to attempt easiness and speediness of a surgical procedure.

The medical device is preferably constructed such that when operating the device with a single hand, the state in which the sticking member protrudes from a distal portion of a catheter is locked by a lock mechanism. Thus, the sticking state of the sticking member can be more reliably maintained so that it is possible to perform the surgical procedure relatively accurately and also smoothly.

The lock mechanism can include a bump member which restricts the slide move of the sticking steering-lever, with the bump member position-fixed on the distal side of a slide groove which is formed at the main body portion and in which the sticking steering-lever slides. The locked state is thus realized by a relatively uncomplicated and simple mechanism in a manner avoiding a large-scale size. Also, quite good steerability can be realized.

A holding-portion locking mechanism is preferably provided for position-fixing the main operation rod at a slide portion provided freely advancingly and retractingly with respect to the main body portion, and the sandwiching of aforesaid sandwiching member and the contact with aforesaid contact member of aforesaid terminal are to be performed in a lump by advancing and retracting aforesaid slide portion with respect to aforesaid main body portion. The movement or steering becomes relatively easy and it is possible to attempt to simplify the surgical procedure.

The holding portion can include a curving mechanism for curving the distal portion of main operation rod by the main operation rod advancingly and retractingly in the axis direction and with respect to this curving mechanism, with a distal sleeve body mounted at the distal end of aforesaid main operation rod and aforesaid main tube being interlocked by a first elastic wire and a second elastic wire. It is thus possible to perform a positioning and holding operations concurrently. Also, a relatively simple construction is achieved and the surgical procedure becomes easier. Also, using a guiding catheter for guiding the catheter that has a curved distal end, it is easier for the catheter, regardless of the state of the foramen ovale valve and the atrial septum secundum which differ depending on the persons, to move toward the foramen ovale between the foramen ovale valve and the atrial septum secundum compared with a case of a straight shape, and safety, usability and speediness of the surgical procedure are improved.

According to another aspect, a medical device comprises a catheter configured to be positioned in a blood vessel, a sticking member having a sharp distal end for sticking biological tissue at a periphery of a defect existing in a biological tissue, with the sticking member movably positioned in the catheter, a sandwiching member cooperating with the sticking member to sandwich the biological tissue between the sticking member and the sandwiching member to close the defect, with the sandwiching member movably positioned in the catheter, an electric supply source for supplying electrical energy, and first and second contact members each electrically connected to the electric supply source. A movable sticking moving-member is connected to the sticking member so the sticking moving-member and the sticking member move together and movement applied to the sticking moving-member causes movement of the sticking member. A movable sandwiching moving-member connected to the sandwiching member so the sandwiching moving-member and the sandwiching member move together and movement applied to the sandwiching moving-member causes movement of the sandwiching member. A first terminal is connected to the sticking moving-member so the first terminal and the sticking moving-member move together, and a second terminal is connected to the sandwiching moving-member so the second terminal and the sandwiching moving-member move together. The sticking moving-member is movable to move the sticking member to a sticking state in which the sharp distal end of the sticking member penetrates the biological tissue, and the sandwiching moving-member is movable to move the sandwiching member to a sandwiching state in which the sandwiching member cooperates with the sticking member in the sticking state to sandwich the biological tissue between the sticking member and the sandwiching member to close the defect. The first terminal contacts the first contact and the second terminal contacts the second contact during the sandwiching state so that electrical energy from the electric energy supply is supplied to the sticking member and the sandwiching member to fuse together the biological tissue sandwiched between the sandwiching member and the sticking member.

According to another aspect, a medical device includes a catheter configured to be positioned in a blood vessel, a sticking member movably positioned in the catheter and possessing a sharp distal end to penetrate biological tissue at a periphery of a defect existing in the biological tissue, the sharp distal end of the sticking member penetrating the biological tissue by entering the biological tissue from one side and exiting the biological tissue at an opposite side, a housing positioned proximally of the catheter, a manually operable sticking moving-lever movably mounted on the housing and connected to the sticking member by way of a sticking moving-member so that manual operation of the sticking moving-lever results in movement of the sticking member by way of the sticking moving-member to position the sticking member in a penetrating state in which the sticking member penetrates the biological tissue, the sticking moving-member extending from the housing to an interior of the catheter, a movable operation rod possessing a distal end configured to contact the opposite side of the biological tissue to hold the opposite side of the biological tissue as the sticking member penetrates the biological tissue, an operation lever movably mounted relative to the housing, and a lock mechanism mounted in the operation lever and through which the operation rod passes, the lock mechanism including a movable engaging member movable between an unlocked position in which the engaging member permits the operation rod to move relative to the operation lever to move the distal end of the operation rod into contact with the opposite side of the biological tissue to hold the opposite side of the biological tissue, and a locked position in which the engaging member holds the operation rod against movement relative to the operation lever to fix the distal end of the operation rod in position to hold the opposite side of the biological tissue as the sticking moving-lever is moved to the penetrating state in which the sticking member penetrates the biological tissue from the one side.

BRIEF DESCRIPTION OF THE DRAWING FIGURES

FIGS. 17A and 17B are schematic views showing another example of a positioning hold mechanism, in which FIG. 17A shows a state at a normal time and FIG. 17B shows a state when holding the positioning.

DETAILED DESCRIPTION

Figure 1:
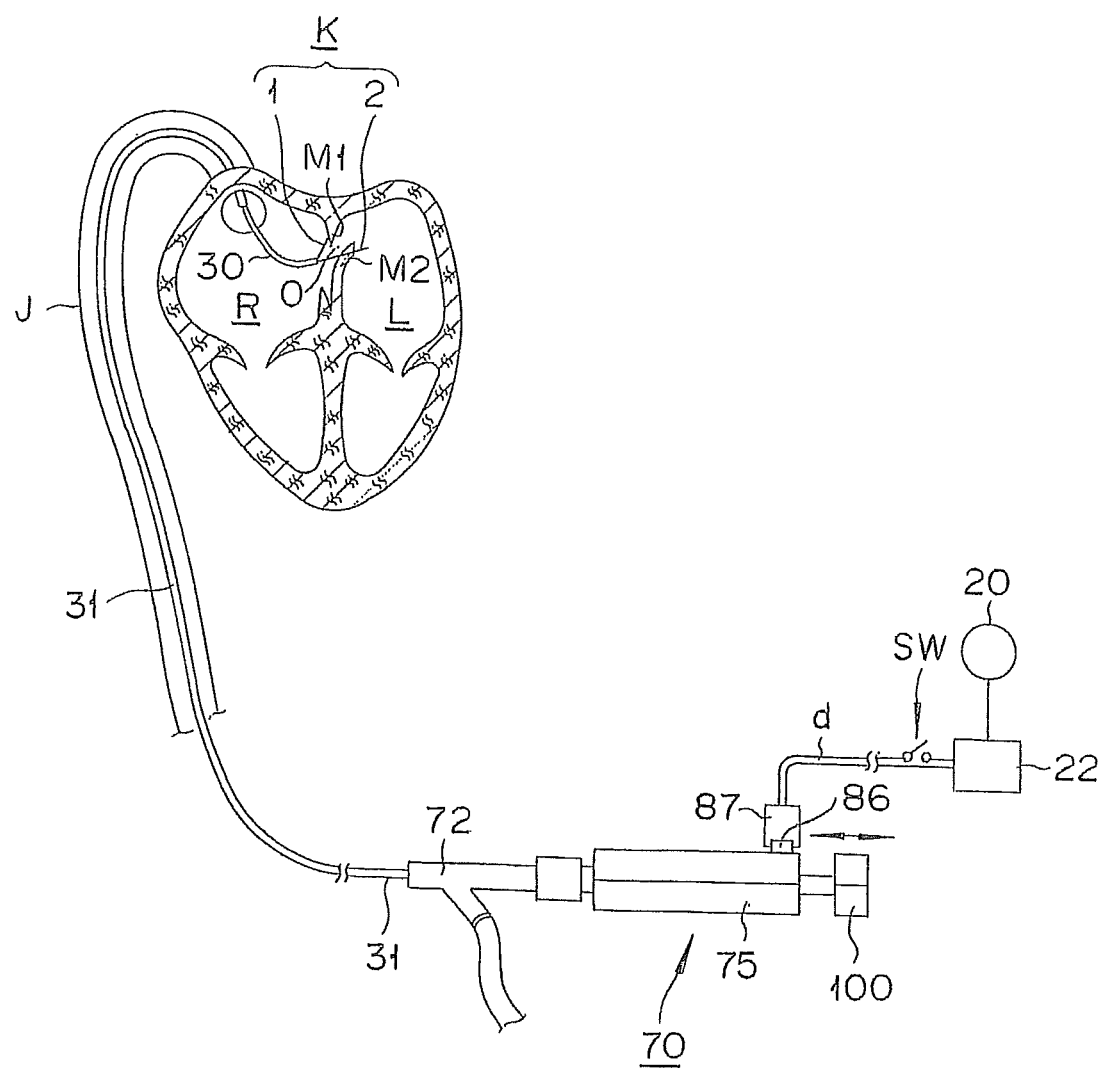
FIG. 1 is a schematic partial cross-sectional view of a medical device according to one embodiment disclosed here.
Figure 2:
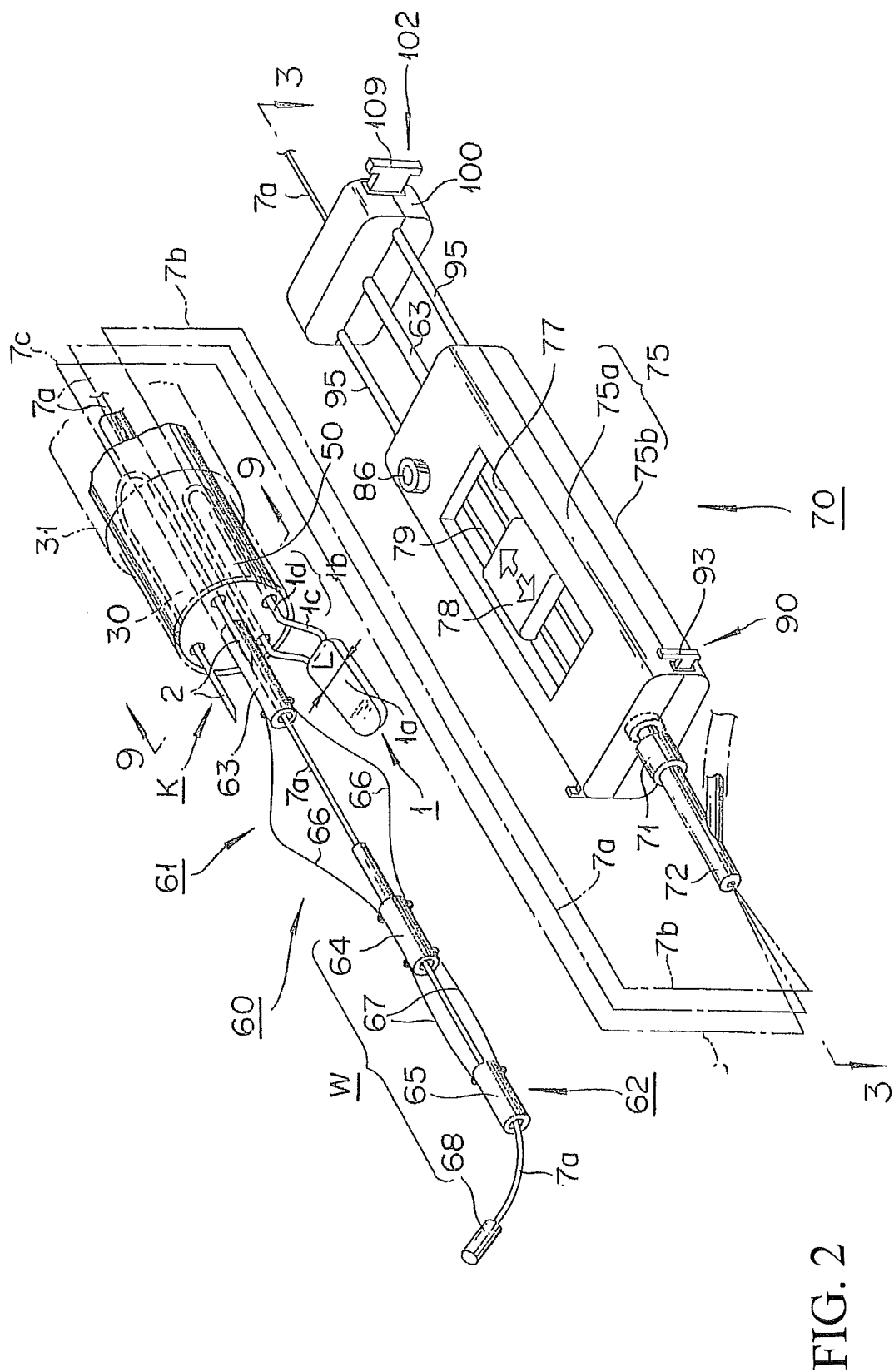
FIG. 2 is a perspective view of a portion of the medical device shown in FIG. 1.

A medical device according to one embodiment is described below with reference to FIGS. 1-13. This device is a device which is used mainly for closing PFO. As shown in FIGS. 1 and 2, the medical device includes a steering unit or moving unit 70 provided on the proximal side, a guiding catheter 31 whose proximal end is mounted on the steering unit 70, a catheter 30 positioned in the guiding catheter 31, clamping means K at a distal portion of the catheter 30 which sandwiches a foramen ovale valve M2 and an atrial septum secundum M1, energy supply means (energy supply source or unit) 20 for supplying energy to fuse or join biological tissue M (generic term for M1, M2) of a portion sandwiched by the clamping means K, and positioning hold means 60 for performing the surgical procedure by the clamping means K stably and accurately. In the following explanation, the side (end) of the device at the steering unit end is referred to as the "proximal side" and the side of the device at the clamping means K end is referred to as the "distal side". Due to space limitations, only the steering or moving unit 70 is illustrated in FIG. 2.

During use, this device is first inserted, for example, from a femoral vein J in a state in which there is housed, in a guiding catheter 31, the whole clamping means K which is provided at the distal end of the catheter 30. Once the distal end reaches the region of the heart at which the procedure is to be performed, the clamping means K protrudes from the distal end of the guiding catheter 31 and the clamping means K sandwiches the tissues of the atrial septum secundum M1 and the foramen ovale valve M2 of the heart having the defect O of the foramen ovale. In this sandwiched state, the clamping means K is supplied with electric energy, both the tissues are heated and fused, and the defect O is closed. In FIG. 1, "L" denotes a left atrium and "R" denotes a right atrium.

Aspects of the medical device will now be described in more detail. The clamping means K comprises, as shown in FIG. 2, by a sandwich member 1 configured to directly contact one side surface of the atrial septum secundum M1 and a sticking member 2 configured to be stuck into the foramen ovale valve M2. The sandwich member 1 and the sticking member 2 function as electrode members respectively, and the proximal portions sandwich member 1 and the sticking member 2 function are held by or secured to a holder 50 located at the distal end of the catheter 30. The sandwich member 1 and the sticking member 2 function are positioned and arranged so they face each other while projecting from the holder 50.

The sandwich member 1 is a flat board portion 1a possessing a flat plate shape and having a predetermined width L, and a pair of wire portions 1b, forming a U-shaped wire member, connected to the proximal portion of the flat board portion 1a. A one-piece steering-member 7b is connected to the proximal side of the U-shaped wire member 1b. Moving the steering-member 7b in the forward axial direction moves the sandwich member 1 forward to protrude from the distal end of the catheter 30, and moving the steering-member 7b in a retreating (rearward) axial direction displaces the sandwich member 1 so it approaches the stick portion 2 side by virtue of the shape of the wire members 1b.

Each wire member 1b includes a bend portion 1c and a straight-shaped portion 1d. The straight-shaped portions 1d are positioned in respective lumens L3, L4 (see FIG. 9) of the holder 50 so as to be movable forward and backward. If the moving-member (operation member or rod) 7a is moved or pulled rearwardly (proximally), it is possible, when the bend portions 1c move into the entrance portion of the lumens L3, L4 of the holder 50, to displace the sandwich member 1 so it approaches the sticking member 2. It is thus possible to relatively easily and smoothly carry out sandwiching of the biological tissue by both electrode members, even in the case of the distal portion of the fine catheter 30.

A SUS material may be used to fabricate the sandwich member 1. It is preferable to use a material for the flat board portion 1a which fulfills a function as the electrode and which does not exert bad influence to a living body such as, for example, the material mentioned above as well as gold, silver, platinum, tungsten, palladium or alloys including these, Ni—Ti alloy, titanium alloy and the like.

The sticking member 2 is held by lumens L1, L2 formed in the holder 50 so as to be movable forward and backward. The sticking member 2 is movable to be extended in the distal (forward) direction from the holder 50 by operating a moving-member (steering-member) 7c connected to the proximal side and is also movable in the rearward direction.

As shown in FIG. 2, the sticking member 2 is comprised of two very fine needle-shaped members whose cross-sections perpendicular to the axes are circles and whose distal ends are sharply pointed. The two needle-shaped members are arranged in spaced apart relation at their distal ends. If the foramen ovale valve M2 is stuck by the sticking member 2, it is possible, even for various forms/shapes/sizes of the foramen ovale valve and the atrial septum secundum, to execute positioning of at least one electrode member relative to the foramen ovale valve M2, and the sandwich operation of the biological tissue M is relatively easy.

It is not always necessary for the sticking member 2 to be a solid cylindrical needle member, as it is possible to employ a hollow cylindrical shaped member, and it is preferable for the outer diameter of the sticking member to be around 0.1 mm to 2 mm in order to be installed in the catheter 30. The material forming the sticking member 2 s preferably a SUS material, though it is also possible to use a material which does not exert a bad influence on a living body such as, for example, gold, silver, platinum, tungsten, palladium, titanium or alloys including these, Ni—Ti alloy and the like. Though not limited in this regard, it is preferable if the mutual distance between the two pieces forming the sticking member 2 is selected such that the foramen ovale valve M2 and the atrial septum secundum M1 can be sandwiched in a certain range. Also, the sticking member 2 is not limited to a construction that only includes tow needle-shaped members as a larger number of pieces than two may be employed.

As the steering-members 7b, 7c for moving the sandwich member 1 and the sticking member 2 in/out from the catheter 30, any kinds of members can be employed if they are fine wire-shaped members, can move the clamping means K forward and backward in the catheter 30, and exhibit electrical conductivity. For example, it is preferable to use a wire such as stainless steel, Ni—Ti, titanium and the like. Both the steering-members 7b, 7c are positioned in the catheter 30 and are connected with the energy supply unit 20 through a coupler 87 engaged with a connector portion 86.

In the clamping means K, the sticking member 2 and the sandwiching member 1 are in a state in which they are respectively movable independently in the axis line direction with respect to the catheter 30. In this manner, if the sticking member 2 and the sandwiching member 1 are constructed to be movable mutually independently by using the steering-members 7b, 7c, the sticking can be carried out at an arbitrary position in the sticking member 2, the surgical procedure in response to the situation of the biological tissue M becomes easier and smoother, and in the sandwiching member 1, movement or steering for pressing the atrial septum M1 with respect to the foramen ovale valve M2 in a stuck state and positioning of the biological tissue M in the thickness direction become possible.

Figure 9:
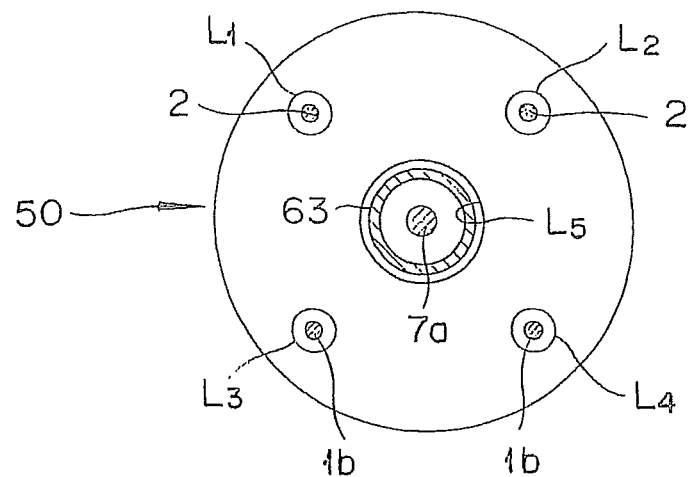
FIG. 9 is a cross-section view along a 9-9 line in FIG. 2.

It should be noted that the holder 50 includes, as shown in FIG. 9, a plurality of lumens L1-L5, but it is also possible that these respective lumens L1-L5 can be constructed as catheters respectively.

Figure 3:
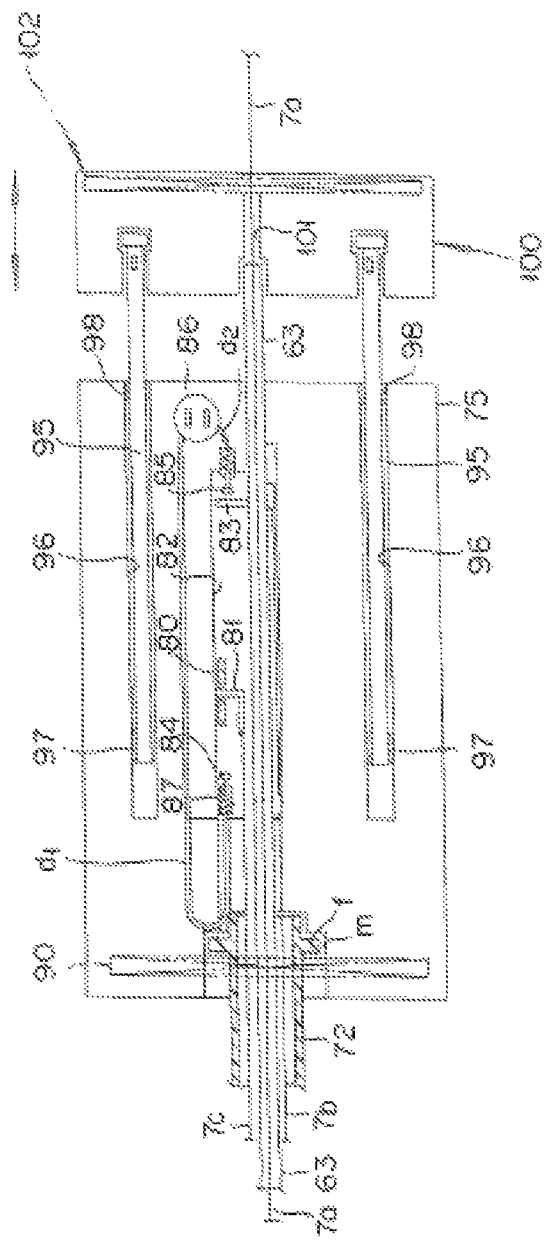
FIG. 3 is a cross-section view along the section line 3-3 in FIG. 2.

A steering unit 70, as shown in FIG. 1 to FIG. 3, includes a main body portion or housing 75 having a flat hollow box shape and a slide portion 100 configured to be freely advanced and retracted so as to approach and be separated from the main body portion 75.

The main body portion 75 is composed of a pair of upper and lower cases 75a, 75b which are aligned face to face, a main tube 63 which passes through an internal space 76 (see FIG. 4) of the main body portion, terminals 81, 83 positioned in the interior of the main body portion, and moving-members (steering-members) 7a, 7b, 7c and the like which are housed in and pass through the interior of the main body portion.

Figure 5:
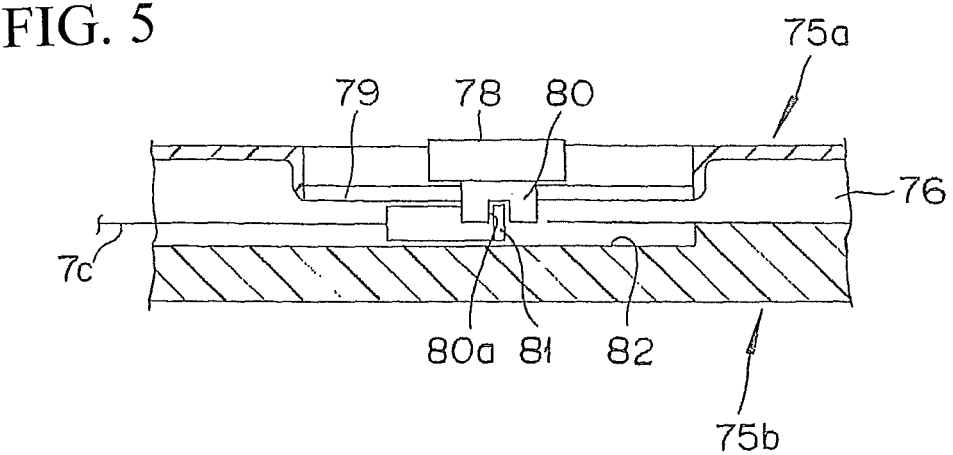
FIG. 5 is a vertical cross-section view of a sticking steering-lever portion generally shown in FIG. 3.

To explain in more detail with reference to FIG. 2, the upper surface side of the upper case 75a is provided with a comparatively wide concave groove 77 in the center of the upper case. A sticking moving-lever is positioned in the groove 77 and is slidable in the longitudinal direction as indicated by the arrows on the sticking moving-lever 78 shown in FIG. 2. The sticking moving-lever 78, as shown in FIG. 5, includes a bracket 80 which protrudes downwardly to reach the internal space 76 by passing-through a slit 79 (see FIG. 2) formed on the upper case 75a. As shown in FIG. 5, an L-shaped terminal 81 provided at the proximal end of a sticking moving-member 7c is engagement-interlocked to a concave portion 80a at the lower end of the bracket 80. Consequently, when the sticking moving—lever 78 is slid along the slit 79, the terminal 81 is, as shown in FIG. 3, slid along a guide groove 82 formed on the lower case 75b such that the sticking member 2 is advanced and retracted through the sticking moving-member 7c.

As shown in FIG. 3, the main tube 63 passes through in the center of the width direction of the upper surface of the lower case 75b. This main tube 63 will be explained in detail later. Generally speaking though, the main tube 63 is a tube which exerts a sort of center-axis like function of this device, and the proximal side of the main tube 63 is interlocked to the slide portion 100 in a position-fixed manner by an adhesive agent or the like. The main tube 63 slides by being guided by both the cases 75a, 75b in response to the slide action of the slide portion 100.

On the main tube 63 in the internal space 76, there is mounted an L-shaped terminal 83 in the vicinity of the left end and it is constructed such that the terminal 83 will slide along with the slide of the main tube 63. To the terminal 83, there is connected a sandwiching moving-member 7b, and the sandwiching moving-member 7b is passed-through therein by passing a side portion of the main tube 63.

Consequently, the slide portion 100 is a portion for moving (steering) the main tube 63 in an advancing and retracting manner, and concurrently, and also serves as a sandwiching moving-lever which moves or steers the sandwiching member 1 by way of the sandwiching moving-member 7b.

The terminal 83 moves by way of the main tube 63 along with the slide of the slide portion 100 which is this sandwiching moving-lever, and the terminal 81 mentioned above moves through the moving-member 7c along with the sliding movement of the sticking moving-lever 78. At the respective movement end positions of the terminal 81 and the terminal 83 are contact members 84, 85.

Figure 4:
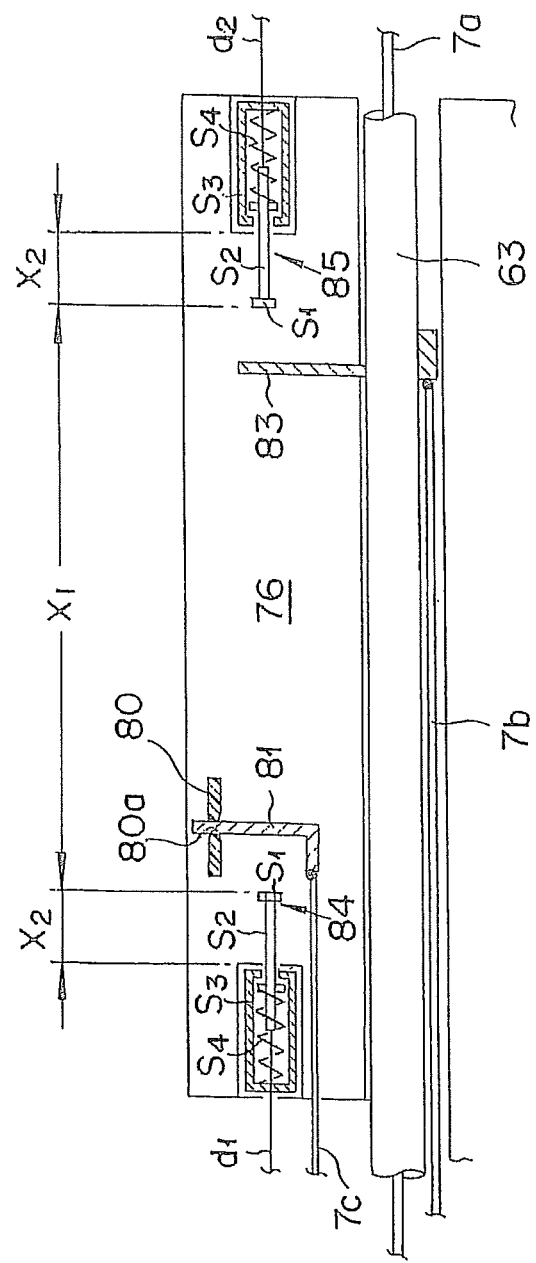
FIG. 4 is a somewhat schematic illustration of contact members and terminals of the device shown in FIG. 1.

The contact members 84, 85 are connected with the connector portion 86 of the energy supply means 20 through the conductive wires d1, d2 and they are provided at mutually separated positions in the steering unit 70, as shown in FIGS. 3 and 4. The reason why the contact members 84, 85 are installed separately in this manner is because a predetermined length X1 (see FIG. 4) is necessary as the working distance thereof caused by a fact that the sticking member 2 and the sandwiching member 1 carry out the sticking and the sandwiching operations by the movement in the axis direction of the moving-members 7c, 7b.

In particular, the contact members 84, 85 of this exemplified embodiment are constructed to contact the terminals 81, 83 respectively before reaching the moving completed positions of the terminals 81, 83 which move along with the movement of the sticking moving-member 7c and the sandwiching steering-member 7b. Also, a switch SW (see FIG. 1) for on-off controlling electric current from the energy supply means 20 is provided at either one of the conductive wires d1 and d2. It is preferable for the switch SW to be provided at the steering unit 70 itself or in the vicinity thereof so as to make it possible to be steered easily, but it is also possible for the switch to be a foot switch installed at the feet.

The contact members 84, 85 will now be explained in more detail. As shown in FIG. 4, the contact members 84, 85 include contact portions S1 which contact the terminals 81, 83, leg portions S2 protruding from the contact portions S1, tubular collars S3 in which the protruding ends of the leg portions S2 are housed, and springs S4 for spring-biasing the leg portions S2 toward the outside. Consequently, the respective contact portions S1 always protrude outwardly by the springs S4 and retreat into the collars when pushed by the terminals 81, 83, so that they are movable over conductable ranges X2 of predetermined lengths as shown in FIG. 4.

With this construction, even if a sticking state of the sticking member 2 or a sandwiching state of the sandwiching member 1 varies depending on, for example, the thickness or the shape of the foramen ovale valve M2 which may vary depending on the person so that the moving completed positions of the terminals 81, 83 vary, the contact members 84, 85 are able to reliably contact the terminals 81, 83. Thus electrical conduction becomes possible and reliability of the surgical procedure is secured. Also, there are members having a construction in which an electrical contact state is formed slidingly, but when compared with such members, the contacts between the contact members 84, 85 and the terminals 81, 83 is quite reliable and potential difficulties become fewer. With respect to the slide operation of the terminals 81, 83, the frictional resistance force becomes less and lighter.

However, it is not necessary for all the groups of contact members 84, 85 and the terminals 81, 83 to be in elastic contact states, and it is possible to employ the state at least for only one group of contact members, and it is also possible to employ a construction in which the other contact member is always in a contact state.

As shown in FIG. 3, a coupling mechanism 90 is provided at the left end portion of the main body portion 75. The coupling mechanism 90 is a mechanism for making attachment and detachment of a Y-connector 72 easy with respect to the main body portion 75. When engaging a flange portion f at a proximal portion of the Y-connector 72 with a ring shaped groove m on the main body portion 75, a pair of slide members 91 which are arranged to face each other (see FIG. 6) exert a pull-off stop function of the flange portion f, and the Y-connector 72 becomes attachable and detachable.

It is preferable for the Y-connector 72 which can be injected with a contrast media or the like to be interlocked to the distal end of the steering unit 70 by an interlock member 71, but in case of not using the Y-connector 72, it happens that the guiding catheter 31 having the flange portion f is to be directly interlocked to the main body portion 75. It is also possible for the Y-connector 72 to be provided at an arbitrary position of the guiding catheter 31.

Figure 6:
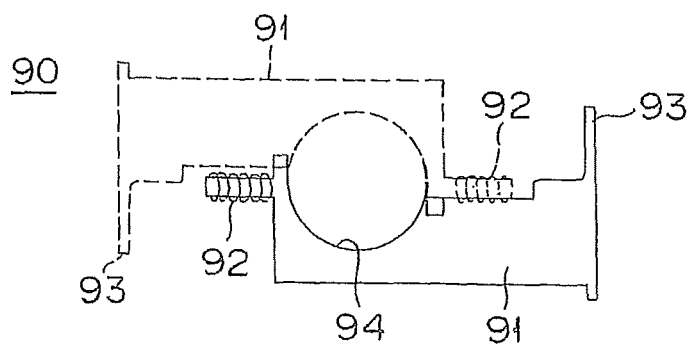
FIG. 6 is a schematic view of a coupling mechanism forming a part of the device shown in FIG. 1.

FIG. 6 is a schematic view of the coupling mechanism and here, in order to make the understanding thereof easier, one of the slide members 91 is shown by a solid line and the other is shown by a broken line.

The coupling mechanism 90 is a mechanism in which the slide members 91 which are a pair of flat plates with similar shapes are adjacently and mutually arranged. Both the slide members 91 are housed so as to be slidable in the direction perpendicular to the axis at the left end portion of the main body portion 75 such that they approach each other by being spring-biased by means of spring members 92 at the distal ends. Consequently, when pushing the end portions (pushers) 93 of both the slide members 91 toward the inner side against the spring members 92, a through-hole 94 with a size by which the flange portion f can pass therethrough exists in the center and it is possible to pass-through the flange portion f. Upon releasing the pushers 93, the through-hole 94 is narrowed by the spring members 92 and it is possible to hold the Y-connector 72, the guiding catheter 31 and the like so as not to be disengaged from the main body portion 75.

As shown in FIG. 3, both sides of the side end regions of the main body portion 75 are provided with grooves 96 that receive a respective guide bar 95 for advancing and retracting the slide portion 100 with respect to the main body portion 75. One terminal end of each guide bar 95 includes a large diameter portion 97 for pull-off stop, and they are constructed so as to stop upon engaging stopper members 98 provided at the outer end portions of the grooves 96.

The guide bars 95 extend from the main body portion 75 toward the slide portion 100, and the end portions of the guide bars 95 interlock with the slide portion 100 by concave-convex engagement as shown in FIG. 3.

The main operation rod 7a passing-through the main tube 63 extends to the outside of the main tube 63 by passing-through a through-hole 101 formed in the center of the slide portion 100. An exit portion of the slide portion includes a locking mechanism (holding-portion locking mechanism) 102 that engages and releases engagement of the operation rod 7a.

Figure 7:
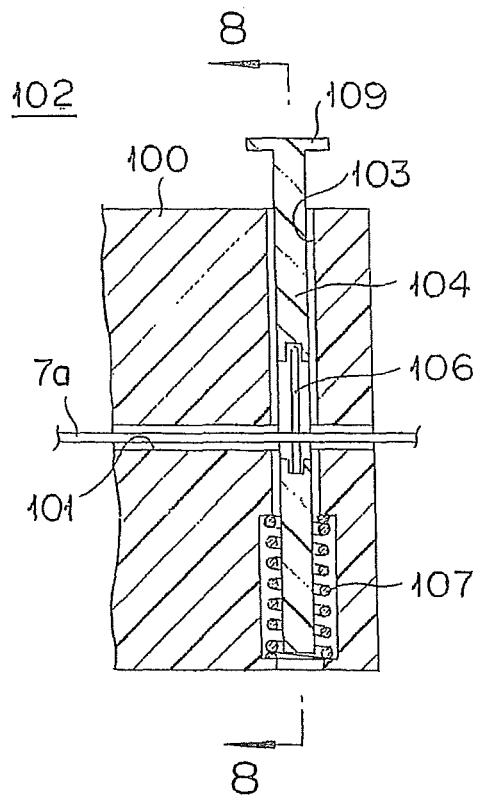
FIG. 7 is a cross-section view of a holding-portion locking mechanism forming a part of the device shown in FIG. 1.
Figure 8:
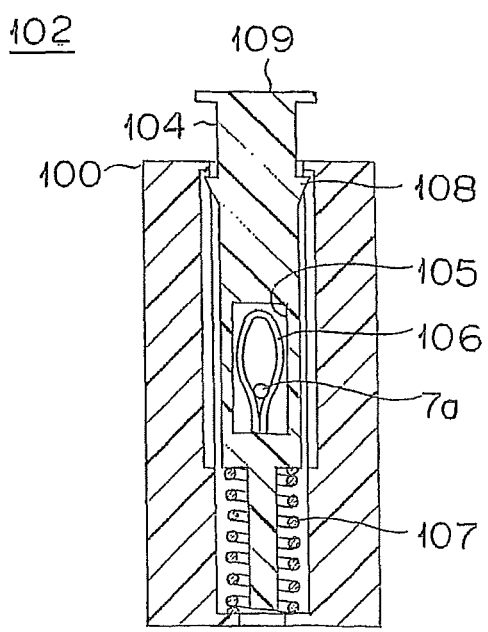
FIG. 8 is a cross-section view along the section line 8-8 in FIG. 7.

FIGS. 7 and 8 illustrate aspects of the holding-portion locking mechanism. The holding-portion locking mechanism 102 is positioned at the slide portion 100 of the steering unit 70. The holding-portion locking mechanism 102 includes a rod grasping member 106 for grasping the main operation rod 7a and a slide stick 104 for releasing the grasping by the rod grasping member 106. In the illustrated embodiment, the rod grasping member 106 is a rod grasping spring. The holding-portion locking mechanism 102 restricts the axial direction movement of the main operation rod 7a, depending on the elasticity of a holding portion 60 (described later), by way of the slide stick 104 and the rod grasping spring 106. The holding-portion locking mechanism 102 is constructed to permit selective positioning of the holding-portion locking mechanism 102 to achieve a lock state in which the holding of the biological tissue M by the holding portion 60 is continued and an unlock state in which the lock state is released.

The slide stick 104 is positioned in a slide hole 103 disposed perpendicular to the through-hole 101 through which passes the main operation rod 7a established at the slide portion 100. The rod grasping spring 106 is fixedly installed in a spring holding hole 105 at approximately in the center of the slide stick 104, and the rod grasping spring 106 elastically grasps the main operation rod 7a. The holding-portion locking mechanism 102 also includes an auxiliary spring 107 which applies a biasing force to the slide stick 104 in the slide hole 103 tending to cause the slide stick to protrude outwardly from the slide hole 103, and a stopper member 108 for limiting the extent of protrusion.

In this embodiment disclosed by way of example, the slide stick 104 is a plate shaped stick which moves upward and downward (considered with reference to the FIGS. 7 and 8 views), and the rod grasping spring 106 is a spring having a shape in which the lower end in the drawing is narrower and the upper portion is widened comparatively largely. It is also possible for the slide stick 104 and the rod grasping spring 106 to be any kinds of members forming a working member and a grasping member for performing the grasping and the releasing of the main operation rod 7a.

The slide stick 104 is urged outward (protrudes outward) by the auxiliary spring 107 on a steady basis and produces a locked state in which the rod grasping spring 106 grasps the main operation rod 7a elastically. When a push piece 109 at the outer end (top end) of the slide stick 104 is depressed toward the inner side against the auxiliary spring 107, this locked state is released and becomes an unlocked state in which the main operation rod 7a is in a free state. As a result, if the main operation rod 7a is lock-unlock operated by the holding-portion locking mechanism 102 and, for example, if the holding portion 60 described later is locked in a state of holding the foramen ovale valve M2, it is possible to maintain this holding state and if the lock is released, it becomes in a straight line shape automatically depending on the elasticity possessed by the holding portion 60 and the holding state of the foramen ovale valve M2 can be released.

The energy supply means 20 is an electric supply for supplying electric energy to the clamping means K. A detailed explanation of the energy supply means is not set forth because of the well known nature of such supplies, though it is preferable, regardless of whether a direct current power source or an alternating current power source is employed, to use an electrical power source. However, the energy supply is not limited in this regard as any kind of energy supply means can be employed if it is one which can supply energy capable of fusing the foramen ovale valve M2 and the atrial septum secundum M1 sandwiched by the clamping means K depending on the heat and the ability to press and attach them taking into account, for example, an adhesive factor of collagen, elastin or the like. For example, it is also possible to use supersonic waves, lasers, microwaves, high frequencies or the like.

Also, as the electric energy supply system, it is possible to use a monopolar system in which electric conduction is executed between the sticking member 2 or the sandwiching member 1 on the right atrium R side and a counter-electrode plate provided on the surface of the body, a bipolar system in which electric conduction is executed between the sandwiching member 1 on the right atrium R side and the sticking member 2 on the left atrium L side, and the like. If a bipolar system is used in which the electric current is controlled by impedance of the biological tissue between the sticking member 2 and the sandwiching member 1, it is possible to have correspondence relatively easily in response to a state of the tissues of the foramen ovale valve M2 and the atrial septum secundum M1 which are different depending on the individual, and there can be obtained advantages of safety and usability of the surgical procedure.

The holder 50 is illustrated in cross-section in FIG. 9, with the illustration of the catheter 30 and the like omitted. The holder 50 includes five lumens L1-L5. As described above, the sticking member 2 passes through the first and second lumens L1, L2, and the sandwiching member 1 passes through the third and fourth lumens L3, L4. The main tube 63 passes through the fifth lumen L5 which is in the center and whose aperture diameter is maximum (i.e., larger than the other four lumens Li-L4). Also passing through or housed in the fifth lumen L5 is the positioning hold means 60.

As shown in FIG. 2, the positioning hold means 60 generally includes a positioning portion 61 for positioning the sticking member 2 with respect to the foramen ovale O and a holding portion 62 for holding the foramen ovale valve M2 non-retractably with respect to the sticking direction of the sticking member 2. The positioning portion 61 is housed in the guiding catheter 31 on a steady basis, but when used, as shown in the drawing, it is pushed out from the guiding catheter 31 by steering or moving the main operation rod 7*a* and the main tube 63.

To explain in more detail, the main tube 63 and the main operation rod 7*a* are positioned in the center lumen L5. The main operation rod 7*a* is positioned in the main tube 63 for free advancing and retracting movement in the axis direction. Other than serving as a tube for pulling-in and withdrawing the positioning hold means 60 relative to the catheter 30, the main tube 63 is a tube functioning as the center axis as mentioned above and also is a tube for reinforcing the catheter 30.

The distal portion of the main tube 63 is provided with the positioning hold means 60, and the positioning hold means 60 is comprised of the positioning portion 61 and the holding portion 62.

The positioning portion 61 is operated in an expanding and contracting manner by the steering or movement of the main operation rod 7*a*. The positioning portion 61 includes a pair of first elastic wires 66 interlocking with (fixed to) the main tube 63 and a middle sleeve body 64. The positioning portion 61 positions the sticking member 2 with respect to the foramen ovale O.

The holding portion 62 includes a bump member 68 at a distal end portion of the main operation rod 7*a*, a distal sleeve body 65, and a pair of second elastic wires 67 interlocking with (fixed to) the middle sleeve body 64 and the distal sleeve body 65. Generally speaking, the holding portion 62 holds the foramen ovale valve M2 by virtue of the distal end of the operation rod 7*a* contacting and holding the foramen ovale valve M2. More specifically, the holding portion 62 holds the foramen ovale valve M2 by way of the bump member 68 and the distal sleeve body 65.

The positioning portion 61 protrudes the main operation rod 7*a* from the distal end of the main tube 63, displaces the first elastic wires 66 outward depending on the advancing and retracting operation or movement of the main operation rod 7*a* in the axial direction, depresses the inner edge of the foramen ovale O with approximately equal elastic force by the respective first elastic wires 66, and center-aligns the sticking member 2 with respect to the foramen ovale O. In other words, the positioning portion 61 functions to position the sticking member 2, located between the first elastic wires 66, at a central portion of the foramen ovale O.

The holding portion 62 includes a curving mechanism W for curving the distal portion of the main operation rod 7*a* by advancing and retracting movement or steering of the main operation rod 7*a* in the axial direction. The curving mechanism W curves the holding portion 62 such that the sticking member 2 makes the foramen ovale valve M2 face the sticking direction and exerts a function for holding the foramen ovale valve M2. Here, the curving mechanism W is constituted by the middle sleeve body 64, the distal sleeve body 65, the second elastic wires 67 fixing together the sleeve bodies 64, 65, and the distal end of the operation rod 7*a* (e.g., the bump member 68).

The proximal ends of the first elastic wires 66 are welded to the distal end of the main tube 63, and the distal ends of the first elastic wires 66 are welded to the middle sleeve body 64. On the other hand, the proximal ends of the second elastic wires 67 are welded to the distal end of the middle sleeve body 64 and the distal ends of the second elastic wires 67 are welded to the distal sleeve body 65.

As one example, the first and second elastic wires 66, 67 are preferably metal wires having an outer diameter of around 0.1 mm to 0.5 mm and made of, for example, stainless steel, nickel-titanium and superelastic alloy (for example, Ni—Ti alloy). In addition, it is also possible to inhibit or prevent damage to tissue by coating the metal wire with, or applying to the metal wire, a resin (flexible) tube.

The holding portion 62 is constructed such that the first elastic wires 66 on the proximal side curve prior to the second elastic wires 67 on the distal side, the positioning of the sticking member 2 is carried out, subsequently the main operation rod 7*a* itself is deformed together with the bump member 68 and the distal sleeve body 65, the positioning portion 61 positions the sticking member 2, and thereafter the foramen ovale valve M2 is held.

For this result, it is also possible to use, for example, a construction/method in which there is a wire having higher material stiffness on the second elastic wire 67 side compared with on the first elastic wire 66 side, or a construction/method in which there is an easily deformable portion produced by bend-deforming a portion of the first elastic wire 66 beforehand and in which deformation of the easily deformable portion occurs when a force is applied, the first elastic wire 66 is curved prior to the second elastic wire 67.

With the disclosed construction, by simply retracting or applying a pulling force in the backward direction on the main operation rod 7*a*, the first elastic wire 66 on the proximal side engages or contacts the inner edge of the foramen ovale O and positioning of the sticking member 2 is carried out. Upon further retraction or application of the pulling force, the second elastic wire 67 on the distal side is deformed in a circular arc shape toward the outside radial direction, and so it is possible to hold the foramen ovale valve M2 non-retractably such that it is easier to stick the sticking member 2.

Also, the main operation rod 7*a* is constructed to be rotatable through 360 degrees in the main tube 63 centering around the axial line. With the main operation rod 7*a* rotatable by 360 degrees, it is possible to position-displace the main operation rod 7*a* in a rotating manner when the distal end of the main operation rod 7*a* is inserted until reaching the vicinity of the foramen ovale O. Even if the state of the foramen ovale O is deformed variously, it is possible, regardless of the shape, to pass-through the distal end of the device into the foramen ovale O. The surgical procedure can thus be carried out easier and more speedily.

When advancing and retracting the slide portion 100 with respect to the main body portion 75, it is possible to pull-in the main tube 63 which is fixedly attached to the slide portion 100 into the center lumen L5 of the catheter 30 and along with this operation, it is possible to withdraw the whole positioning hold means 60 into the catheter 30.

For a material constituting the main tube 63, it is possible to use a deformable elastic material such as, for example, polyimide resin, polyurethane, PET, nylon, fluoride resin, polypropylene and the like.

Also, the main operation rod 7a is preferably a rod of a fine hollow wire material or a rod having comparable stiffness. Any kind of rod having such stiffness may be employed, but it is preferable to use a fine tube of, for example, stainless, Ni—Ti, titanium and the like.

With respect to the guiding catheter 31 of this embodiment, it is possible for the distal end of the guiding catheter to be curved gently in a circular arc shape such that it can be more easily directed toward the foramen ovale O between the foramen ovale valve M2 and the atrial septum secundum M1. The foramen ovale valve M2 and the atrial septum secundum M1 differ between individuals, so that when the distal end of the guiding catheter 31 is curved, it can be directed toward the foramen ovale O by simply rotating the guiding catheter 31 itself, with safety and usability of the surgical procedure being improved compared with a case of a straight line shape.

Figure 10:
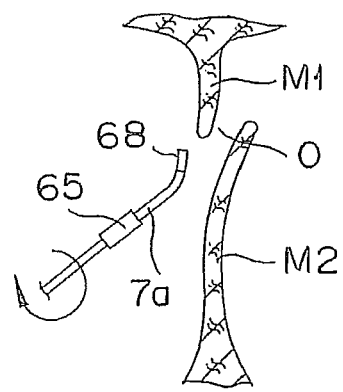
FIG. 10 is a cross-sectional schematic view showing a main operation rod inserted into a defect of a biological tissue.
Figure 11:
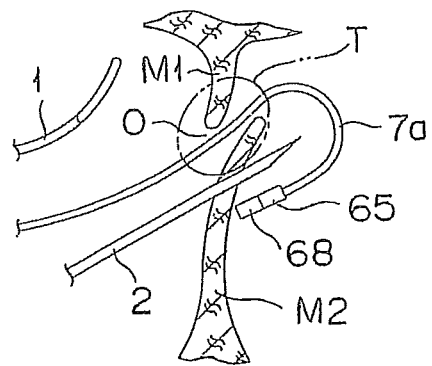
FIG. 11 is a cross-sectional schematic view of a state in which a biological tissue is held and a sticking member is stuck thereto.
Figure 12:
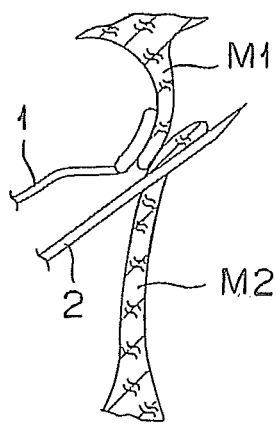
FIG. 12 is a cross-sectional schematic view in which biological tissues are sandwiched by a sticking member and a sandwich member.

The operation of this embodiment is as follows, with reference to FIG. 10 showing the main operation rod inserted into the foramen ovale, FIG. 11 illustrating the foramen ovale valve being held and the sticking member being stuck, FIG. 12 depicting the foramen ovale valve and the atrial septum secundum being sandwiched by the sticking member and the sandwiching member, and FIGS. 13A-13D showing operation states of the distal portion of the PFO closing device. In FIGS. 13A-13D, the shapes and the positions of the second elastic wires 66 are shown in approximately the same-plane with respect to the sandwiching member 1 and the sticking member 2, but the illustrated positions are shown in order to make it easier to understand. The actual positions are displaced by 90 degrees and so it is to be understood that the actual relative positions differ from those illustrated.

First, a surgery operator retracts or rearwardly moves the slide portion 100 of the steering unit 70 with respect to the main body portion 75. This results in a state in which, for example, the sandwiching member 1 and the sticking member 2 are housed in the guiding catheter 31. In this state, by using a guide wire as a guide, the distal end of the guiding catheter 31 is inserted from a predetermined position of a living body and is advanced until reaching the right atrium R through the femoral vein J. It is also possible to insert only the guiding catheter 31 into a living body and thereafter, to insert the catheter 30 by using the guiding catheter 31 as a guide.

When the distal end of the guiding catheter 31 reaches the right atrium R, the slide portion 100 is moved forward a little bit, and the main tube 63 is moved forward, the catheter 30 is pushed out from the guiding catheter 31 and is directed toward the foramen ovale O between the foramen ovale valve M2 and the atrial septum secundum M1. The distal end of the guiding catheter 31 is curved, so that the catheter 30 is guided by the guiding catheter 31 and is directed toward the foramen ovale O comparatively easily.

Figure 13A:
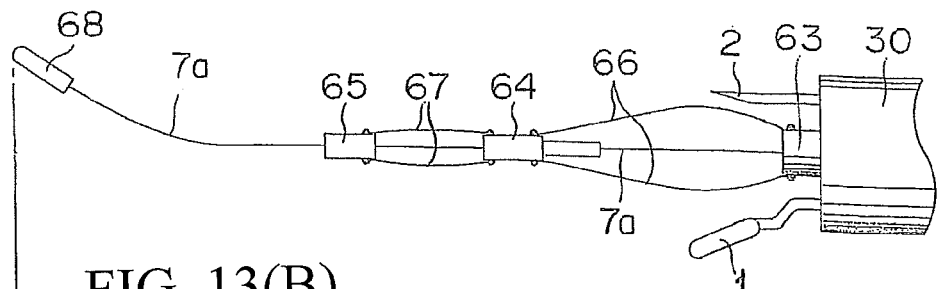
FIG. 13A-FIG. 13D are schematic views showing operation states of the medical device shown in FIG. 1.

Next, the push piece 109 of the holding-portion locking mechanism 102 is pushed and the main operation rod 7a is unlocked (positioned in an unlocked state). The main operation rod 7a is moved forward and, as shown in FIG. 13A, the distal end of the main operation rod 7a protrudes from the distal sleeve body 65 and is inserted into or positioned in the left atrium L. It is possible to visually observe this protruding state according to an X-ray image from the outside if a radiopaque marker is provided on the bump member 68 or the like. It is also possible to identify, using the touch sense, the position of the distal end of the main operation rod 7a when the distal end of the main operation rod 7a bumps against an inner wall of the left atrium L or the like even in a case in which it is difficult to visually observe. In the present embodiment, the main operation rod 7a is rotatable by 360 degrees so that, as shown in FIG. 10, the main operation rod 7a can be moved forward while rotating and it is possible to insert it into the foramen ovale O relatively easily.

Figure 13B:
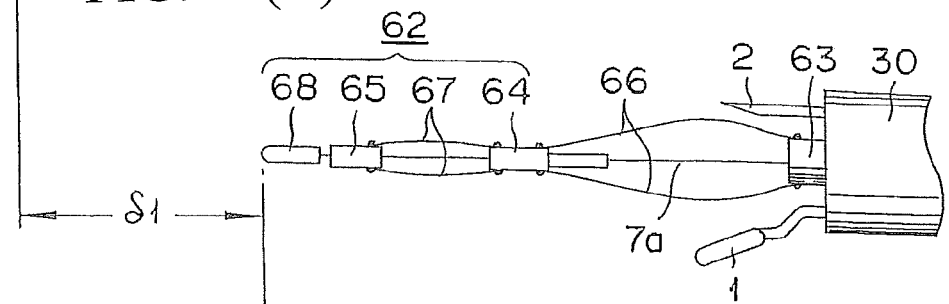

Referring to FIG. 13B, after identifying the distal position of the main operation rod 7a, the main operation rod 7a is moved backward as the bump member 68 of the main operation rod 7a approaches the distal sleeve body 65 (amount of backward movement is "δ1" in FIG. 13B). Then, the main body portion 75 is moved, and the second elastic wire 67, the sandwich member 1 and the sticking member 2 are positioned in the vicinity of the foramen ovale valve M2 and the whole holding portion 62 is inserted into the left atrium L side.

Figure 13C:
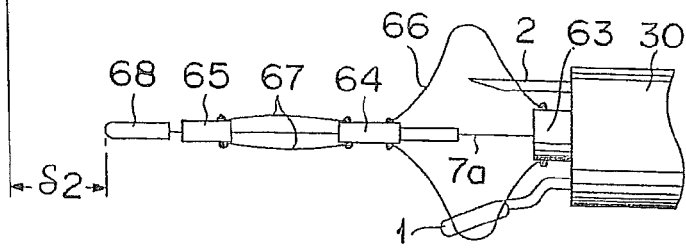

When the main operation rod 7a is further moved backward (amount of backward movement is "δ2" in FIG. 13C), the operation force associated with the backward movement is transmitted by the main operation rod 7a to the first elastic wire 66 firmly fixed on the distal end of the main tube 63 through the bump member 68, the distal sleeve body 65, the second elastic wire 67 and the middle sleeve body 64. The first elastic wire 66, as shown in FIG. 13C, protrudes and is deformed in an arc shape toward the outside direction in the radial direction. However, at this time, the second elastic wire 67 is not deformed.

Consequently, it happens that the first elastic wire 66 is deformed while pushing and widening an opening edge portion of the foramen ovale O, and the sticking member 2 which is in close vicinity of the first elastic wire 66 is center-aligned with respect to the foramen ovale O and the sticking member 2 is positioned at the center of the foramen ovale O.

Figure 13D:
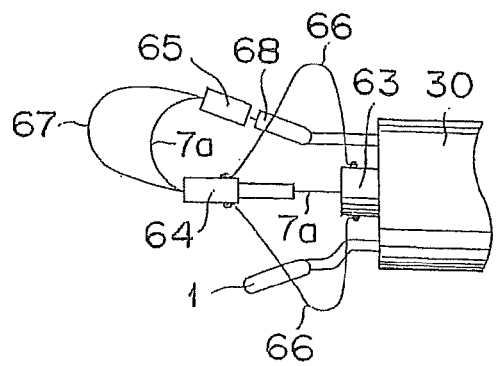

Further, as shown in FIG. 13D, when the main operation rod 7a is further retracted or moved rearwardly, and the rear end of the middle sleeve body 64 approaches the distal end of the main tube 63, the first elastic wire 66 is not deformed much more, but the second elastic wire 67 of the distal side protrudes and is deformed in an arc shape toward the outside radial direction by the operation force. Consequently, as shown in FIG. 11, in the left atrium L, the bump member 68 and the distal sleeve body 65 are curved so as to approach the sticking member 2. It thus happens that the bump member 68 and the distal sleeve body 65 contact the surface of the left atrium side of the foramen ovale valve M2 and hold the left atrium side of the foramen ovale valve M2.

In this valve holding state, if the main operation rod 7a is locked by the rod grasping spring 106 of the holding-portion locking mechanism 102, the position of the main operation rod 7a is locked. Therefore, even if the surgery operator releases his hand from the main operation rod 7a, the holding state of the foramen ovale valve M2 is maintained and it is not likely that the holding state will be loosened. As a result, it is not necessary for the surgery operator to hold down the steering unit 70 by his left hand, and so it is possible for him to move the sticking steering-lever 78 forward in the concave groove 77 only by his right hand to move the sticking member 2 from the distal end of the catheter 30 through the terminal 81 and the steering-member 7c and to stick the sticking member 2 into a predetermined position of the foramen ovale valve M2 (i.e., the sticking member penetrates the foramen ovale valve M2). It is thus possible to avoid a situation in which the sticking is excessively difficult or impossible because of a loose, unsupported state of the foramen ovale valve M2 in which the foramen ovale valve M2 is not held or is held insufficiently.

The position of the sticking member 2 is determined by the positioning hold portion 60, so that there is little concern about deviation. Also, when the sticking member 2 is stuck once, the position of the sticking member 2 becomes a fixed position in relation to the foramen ovale valve M2. Therefore, it is easier for the surgery operator to perform the sticking operation.

In the steering unit 70, by virtue of the sticking operation, a state occurs in which the terminal 81 contacts the contact member 84 elastically. That is, in the sticking state in which the sharp distal end of the sticking member penetrates the biological tissue, the terminal 81 contacts the contact member 84.

In this stage, if the push piece 109 of the holding-portion locking mechanism 102 is pushed and the locked state of the main operation rod 7a by the rod grasping spring 106 is released, pressurization of the first elastic wire 66 and the second elastic wire 67 by the main operation rod 7a and the bump member 68 disappears, the first elastic wire 66 and the second elastic wire 67 are lengthened and move towards a straightened shape by the elastic forces themselves, and they reach a state shown in FIG. 13B. Consequently, when rearwardly moving or retracting the slide portion 100, the whole positioning hold means 60 is retracted by way of the main tube 63 and withdrawn in the lumen L5 of the catheter 30 (i.e., removed from the position shown inn FIG. 11).

With the sticking or penetration by the sticking member completed, the slide portion 100 is moved further forward with respect to the main body portion 75 and when the main tube 63 is moved forward, the flat board portion 1a of the sandwiching member 1 protrudes from the distal end of the catheter 30 by way of the steering-member 7b. Then, when the flat board portion 1a is positioned facing the atrial septum secundum M1, the slide portion 100 is retracted or moved rearwardly a little bit from the main body portion 75. Thus, the flat board portion 1a is displaced so as to approach to the sticking member 2 and presses the atrial septum secundum M1 toward the foramen ovale valve M2, and the atrial septum secundum M1 and the foramen ovale valve M2 contact each other in the thickness direction. That is, the positions of the atrial septum secundum M1 and the foramen ovale valve M2 in the forward-backward direction are fixed in the operation state and, as shown in FIG. 12, a state arises in which the atrial septum secundum M1 and the foramen ovale valve M2 exist between the sandwich member 1 and the sticking member 2.

Also, the retreating movement of this slide portion 100 causes the bend portion 1c of the sandwiching member 1 to move and approach the sticking member 2 side from the end portion of the holder 50 through the steering-member 7b, so that as shown in FIG. 12, the atrial septum secundum M1 and the foramen ovale valve M2 are sandwiched strongly between the sandwiching member 1 and the sticking member 2. On the other hand, in the steering unit 70, the terminal 83 mounted on the main tube 63 is also retreated and contacts the contact member 85.

In other words, it happens that the rearward movement of the slide portion 100 in this stage will effect the sandwiching of the biological tissues M and the contact state of the terminal 83 and the contact member 85 at one time. Furthermore, the terminal 81 and the contact member 84 earlier reached a contact state and so a state arises in which it is possible to supply electric energy to the sandwiching member 1 and the sticking member 2 depending on the contact of the terminal 83 and the contact member 85.

Consequently, when the surgery operator turns on the switch SW, predetermined electric energy controlled by the control unit 22 is supplied to the sandwiching member 1 and the sticking member 2 through the steering-members 7b, 7c, and the atrial septum secundum M1 and the foramen ovale valve M2 are heated.

The control unit 22 controls the output power to be relatively low and makes it difficult for a thrombus to be attached, so that even if a portion of the sandwiching member 1 and the sticking member 2 is exposed in the blood, it is possible to inhibit or prevent the thrombus from being attached to the sandwiching member 1 and the sticking member 2. However, if a coating for suppressing thermal conduction is applied to the surfaces of the sandwiching member 1 and the sticking member 2 which are exposed to the blood, the attachment of a thrombus is reliably inhibited or prevented.

When continuing the heating while maintaining the fusing temperature, the tissues of the atrial septum secundum M1 and the foramen ovale valve M2 melt and are mutually fused together by a bonding factor of collagen, erastin or the like.

When the fusion is completed, the switch SW is turned off, the supply of the electric energy is stopped, the slider portion 100 is moved in an advancing and retracting manner, and the sandwiching member 1 and the sticking member 2 are housed in the guiding catheter 31 by way of the main tube 63. Then, when the main body portion 75 is retreated so as to be away from the living body, the guiding catheter 31 is pulled out from the living body and the surgical procedure is completed. After the completion of the surgical procedure, a very small hole remains in the foramen ovale valve M2 caused by the pulling-out of the sticking member 2, but this very small hole will heal and a bad influence such as occurrence of a thrombus or the like does not occur.

Figure 14:
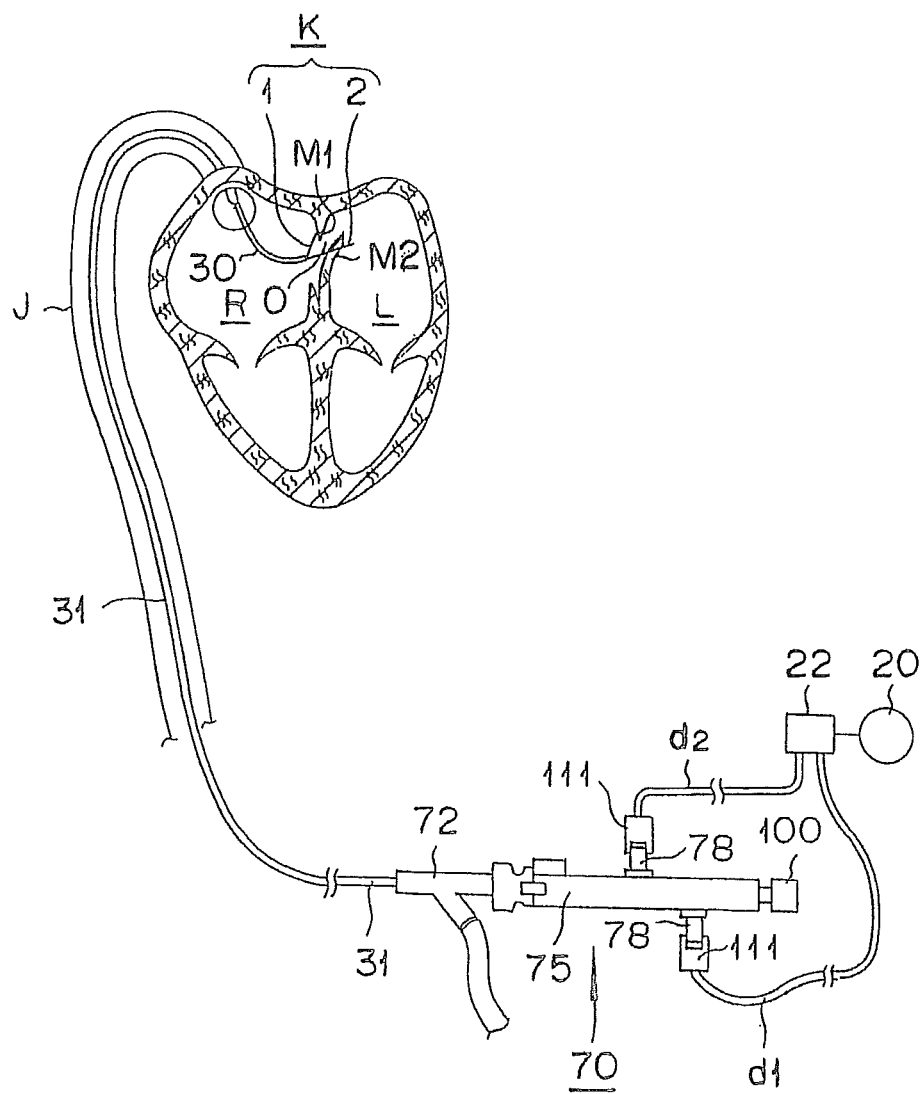
FIG. 14 is a schematic partial cross-sectional view of a medical device according to a second embodiment disclosed here.
Figure 15:
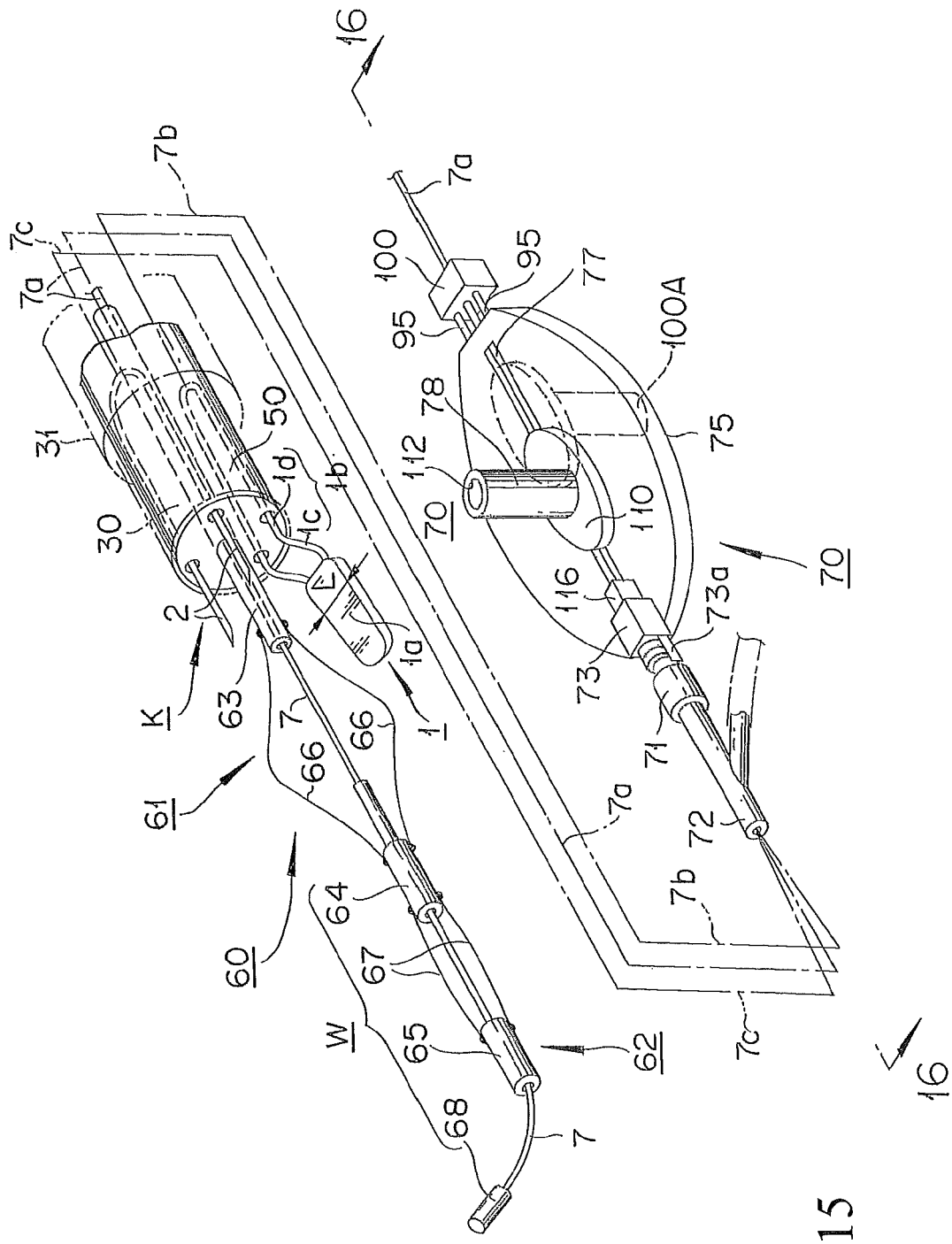
FIG. 15 is a perspective view of a portion of the medical device shown in FIG. 14.
Figure 16:
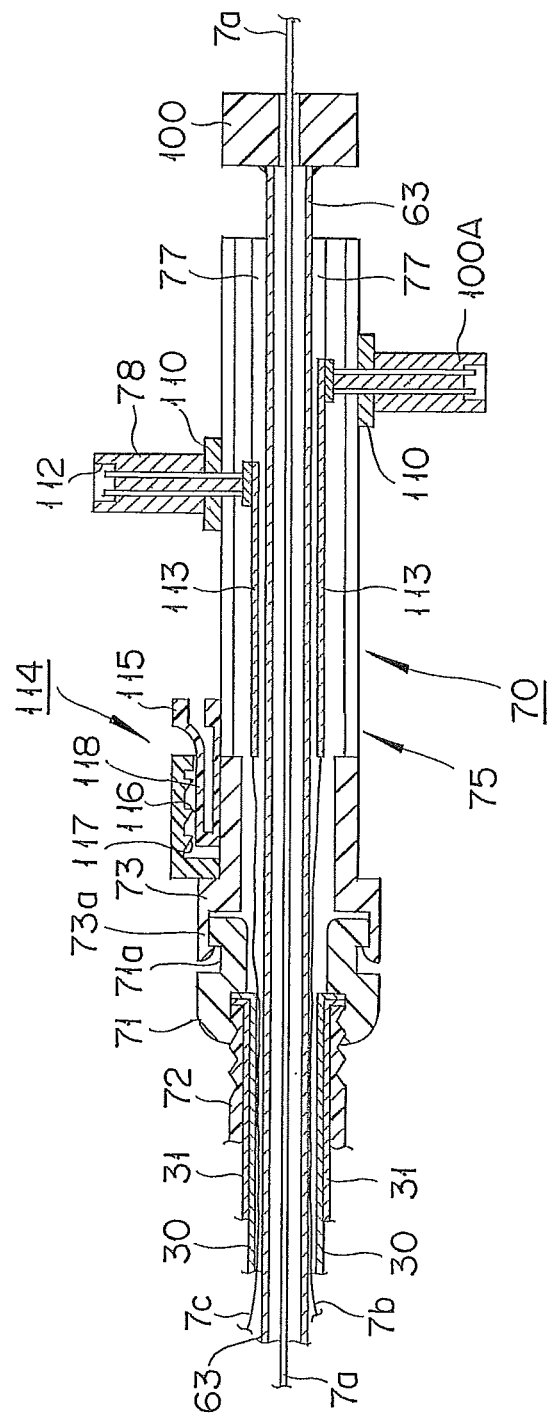
FIG. 16 is a longitudinal cross-sectional view along the section line 16-16 in FIG. 15.

A second embodiment of the medical device is illustrated in FIGS. 14-16. In this embodiment of the medical device, the steering unit 70 includes a portion for controlling the supply of the electric energy and a portion of the steering-lever for steering the sandwiching member 1 and the sticking member 2 which are different from those associated with the first embodiment.

In the first embodiment, the on-off control of the electric energy supply is carried out by a switch SW. This second embodiment does not use a switch SW and the control is carried out by attachment-detachment operation of the sticking moving-lever 78 and a sandwiching steering-lever 100A which are provided at the steering unit 70 with respect to connection members 111 of the electric energy supply means 20 side.

Also, in the first embodiment, the main body portion 75 of the steering unit 70 includes the sticking moving-lever 78 which steers or moves the sticking member 2 on the upper surface thereof, and the sandwiching member 1 is steered or moved by the slide portion 100. On the other hand, this second embodiment is provided with the sticking steering-lever 78 and the sandwiching moving-lever 100A protruding from the upper and lower surfaces of the main body portion 75. features in this second embodiment that are the same as in the first embodiment are identified by the same reference numeral and a detailed description of such features will not be repeated. The description below primarily focuses on differences between this embodiment and the first embodiment.

With respect to the steering or moving unit 70 of this embodiment, as shown in FIG. 14 and FIG. 15, in order to make it possible for the surgery operator to execute the gripping by one hand, the moving-lever 78 protrudes on the front surface side (upper surface side) of the main body portion 75 which is flat-shaped. The moving-lever 78 is interlocked with the proximal end of the sticking moving-member 7c. In addition, protruding from the rear surface side (lower surface side) of the main body portion 75 is the sandwiching moving-lever 100A with which the proximal end of the steering-member 7b of the sandwiching member 1 is interlocked.

As illustrated in FIGS. 14 and 16, the respective moving-levers 78, 100A are slidably positioned in the concave groove 77 formed in the main body portion 75, and the groove is constructed such that the moving-levers 78, 100A can slidingly move quite smoothly without toppling depending on flange portions 110 provided at lower end portions of the respective moving-levers 78, 100A. Also, the end portions of the sticking moving-lever 78 and the sandwiching moving-lever 100A are provided with respective concave portions (recessed regions) 112 which permit the attachment and detachment of electrical connection members 111 of the electric energy supply means 20, such that the on-off control of the electric energy supply is carried out. The free end portions of the sticking moving-lever 78 and the sandwiching moving-lever 100A thus form connectors removably electrically connectable to the electrical connection members 111 of the electric supply source 20.

Consequently, if the surgical procedure by both the moving-levers 78, 100A is carried out and the concave portions 112 of both the moving-levers 78, 100A are connected to the connection members 111 while maintaining the state of sandwiching the biological tissue M, it is possible to supply the electric energy, so that it is possible to realize an electric energy supply at any desired point in time. Also, the conductive wires d1, d2 do not become obstacles during the surgical procedure, and usability and reliability of the steering are improved significantly. Furthermore, it does not happen that the electric energy is supplied to the biological tissue M unnecessarily, and so it is possible to prevent attachment of a thrombus.

It is also possible for the respective moving-members 7b, 7c and the respective moving-levers 78, 100A to be connected directly by soldering or the like. The construction in this embodiment involves the proximal ends of the respective steering-members 7b, 7c being soldered on the distal ends of slide pieces 113 which slide in the concave groove 77 formed in the main body portion 75, electrical conductors provided on the respective moving-levers 78, 100A being soldered on the proximal ends of the slide pieces 113, and these electrical conductors extending through the moving-levers 78, 100A to the respective concave portions 112 which receive the connection member 111 to establish an electrical conduction state with the respective connection members 111. If connection is realized electrically through the slide piece 113 in this manner, the steerability of the device is improved and also the strength or durability is improved.

Also, the steering unit 70 in this embodiment includes, at the distal portion of the main body portion 75, a sticking-member locking mechanism 114 which locks a state in which the sticking member 2 protrudes from the distal portion of the catheter 30.

The sticking-member locking mechanism 114 is a mechanism involving, on the distal side of the concave groove 77 formed in the main body portion 75, a bump member 115 for restricting the slide movement of the sticking steering-lever 78 and which locks the slide movement by pressing the sticking moving-lever 78 onto the bump member 115. When the sticking moving-lever 78 is pressed onto the bump member 115 in a state in which the sticking member 2 protruded from the distal portion of the catheter 30, the position of the sticking moving-lever 78 can be locked and a protrusion state of the sticking member 2 can be maintained. Consequently, it is possible to supply the electric energy while pressing the sticking moving-lever 78 onto the bump member 115, the sticking member 2 does not deviate when supplying the electric energy, and it is possible to carry out the surgical procedure more stably and also more accurately.

FIG. 16 shows an illustrative example of the sticking-member locking mechanism 114. It is a mechanism in which a tubular block 116 is fixed on the main body portion 75 and the bump member 115 is adjustably positioned in the tubular block 116. As a position adjustment means of the bump member 115, a construction is employed in which a plurality of protrusions 117 having non-retractable shapes are provided interiorly in the inner surface of the tubular block 116 and claw portions 118 on the side of the bump member 115 which exhibits elasticity in the radial direction is latched to the protrusion 117. The claw portions 118 are positioned on the side of the bump member 115 facing the protrusions 117.

At the rear end portion of the main body portion 75, the slide portion 100 is provided and connected to two guide bars 95 in a manner similar to the first embodiment and it is constructed such that the main tube 63 will be advanced and retracted by the slide portion 100. However, in this illustrated embodiment, the holding-portion locking mechanism 102 is not provided, though it is to be understood that it is possible to provide the holding-portion locking mechanism 102 in this second embodiment.

At the distal end of the main body portion 75, the Y-connector 72 into which a contrast media or the like can be injected is interlocked through the interlock members 71, 73. The proximal portion of the interlock member 71 is formed with a groove portion, and this groove portion 71a and a claw portion 73a of the interlock member 73 engage each other and are interlocked. The distal portion of the interlock member 71 threadably engages the proximal portion of the Y-connector 72, and the proximal end of the catheter 30 and the end portion of the guiding catheter 31 are sandwiched between the interlock member 71 and the Y-connector 72 as shown in FIG. 16.

The operation of this embodiment will now be explained, though aspects of the operation that are the same as the operation previously described are not repeated.

After adjusting the position of the bump member 115 of the sticking-member locking mechanism 114, the sticking member 2 is stuck to the biological tissue M held by the positioning hold means 60. Depending on this sticking, the sticking moving-lever 78 is engaged with the sticking-member locking mechanism 114, so that when holding this attachment state, the position of the sticking moving-lever 78 is locked and there is little fear that the position of the sticking member 2 will deviate. Consequently, while holding the sticking moving-lever 78, the surgery operator steers the sandwiching moving-lever 100A provided on the lower surface side of the steering unit and executes the sandwiching of the biological tissue M.

With respect to the sandwiching of the biological tissue, first the sandwiching moving-lever 100A is moved forward, by way of the moving-member 7c, so that the sandwiching member 1 protrudes from the distal end of the catheter 30. Thus, as shown in FIG. 11, a state is reached in which the atrial septum secundum M1 and the foramen ovale valve M2 exist between the sandwiching member 1 and the sticking member 2.

Then, when the sandwiching moving-lever 100A is moved rearwardly to retreat, the sandwiching member 1 retreats or moves rearwardly through the moving-member 7c, and the atrial septum secundum M1 and the foramen ovale valve M2 are relatively strongly sandwiched between the sandwiching member 1 and the sticking member 2.

In a state in which the forward position of the sticking moving-lever 78 and the retreat position of the sandwiching moving-lever 100A are maintained, if the connection members 111 are fitted in a concave-convex form with the concave portions 112 of the respective moving-levers 78, 100A, a predetermined electric current controlled by the control unit 22 flows from the sandwiching moving-lever 100A and the sticking moving-lever 78 to the sandwiching member 1 and the sticking member 2 through the moving-members 7b, 7c, and the atrial septum secundum M1 and the foramen ovale valve M2 are heated and fused.

When the fusion is completed, the electrical conduction is stopped by disengaging the connection between the connection member 111 and either one of the moving-levers 78, 100A.

Figure 17A:
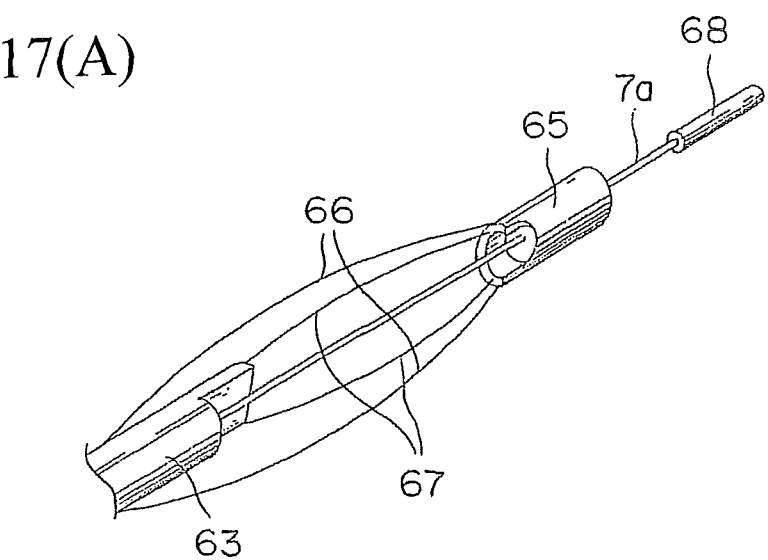
Figure 17B:
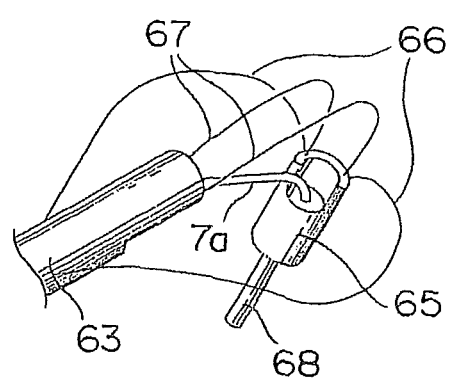

The medical device disclosed here is not limited only by the embodiments disclosed by way of example here. It is possible for a person skilled in the art to employ various modifications within the technical concept of the present invention. For example, the positioning hold means 60 in the embodiment mentioned above includes the middle sleeve body 64, but the present invention is not limited only by this. For example, FIGS. 17A and 17B are schematic illustrations of another example of the positioning hold mechanism. As shown in FIG. 17A, it is also possible to provide the first elastic wire 66 and the second elastic wire 67 between the distal sleeve body 65 and the main tube 63 without providing the middle sleeve body 64 which is provided in the above-described embodiments. In this case, when the main operation rod 7a is moved backward, as shown in FIG. 17B, the second elastic wire 67 is bent and deformed into an arc shape while the first elastic wire 66 protrudes and is deformed in an arc shape in the radial outside direction. More specifically, it happens that the positioning of the sticking member 2 to the center of the foramen ovale O caused by the first elastic wire 66 and the holding of the foramen ovale valve M2 caused by the bump member 68 and the distal sleeve body 65 which are bent by the second elastic wire 67 are to be performed simultaneously based on one action resulting from the backward movement of the main operation rod 7a.

The medical device disclosed here is described as a medical device used for closing the defect of the PFO, but the present invention is not limited only to this usage as it is also possible to use it in a case in which a pathway shaped defect referred to as a left auricle closing device (Left Atrial Appendage) is closed or in a case in which the biological tissue of a predetermined region is necrotized thermally.

With respect to the PFO closing device disclosed here, it is housed in the catheter and steers the clamping means by the steering-member, but it is not limited only by this. For example, it is also possible to carry it to a predetermined position by employing a combination with a so-called catheter having a balloon.

The detailed description above describes various embodiments of a medical device. However it is to be understood that the invention is not limited to those precise embodiments described and illustrated above. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A medical device comprising:
a catheter configured to be positioned in a blood vessel;
a sticking member for sticking a biological tissue at a periphery of a defect existing in the biological tissue, the sticking member being movably positioned in the catheter for movement in an advancing and retracting manner;
a sandwiching member cooperating with the sticking member to sandwich the biological tissue between the sticking member and the sandwiching member to close the defect, the sandwiching member being movably positioned in the catheter for movement in an advancing and retracting manner;
two spaced apart contact members each connected to a conductive wire, connectable to an energy supply source that supplies energy, to supply energy to the contact members;
a movable sticking moving-member connected to the sticking member to move the sticking member in the advancing and retracting manner;
a movable sandwiching moving-member connected to the sandwiching member to move the sandwiching member in the advancing and retracting manner;
a pair of terminals including one terminal and an other terminal, the one terminal connected to one of the sandwiching moving-member and the sticking moving-member so the terminal moves together with the one of the sandwiching moving-member and the sticking moving-member during movement of the one of the sandwiching moving-member and the sticking moving-member, at least one of the pair of terminals not contacting a respective one of the contact members in an initial state;
the other terminal connected to the other of the sandwiching moving-member and the sticking moving-member; and
the sticking moving-member being movable to move the sticking member to stick the biological tissue and the sandwiching moving-member being movable to move the sandwiching member to a position to cooperate with the sticking member in a sandwiching state in which the biological tissue is sandwiched between the sticking member and the sandwiching member to close the defect, the one terminal moving from the initial state to contact one of the contact members in the sandwiching state and the other terminal contacting the other contact member so that with the conductive wire connected to the energy supply source, energy flows to the sticking member and the sandwiching member only in the sandwiching state to fuse together the biological tissue sandwiched between the sandwiching member and the sticking member.

2. The medical device according to claim 1, comprising a switch operable to permit or prevent supply of energy to the sticking member and the sandwiching member.

3. The medical device according to claim 1, wherein the sticking moving-member is connected to a manually operable first lever, and the sandwiching moving-member is connected to a manually operable second lever, the manually operable first lever and the manually operable second lever each including a connector permitting detachable electrical connection to electrical connectors of the energy supply source.

4. The medical device according to claim 1, wherein said at least one of the pair of terminals not contacting a respective one of the contact members in an initial state comprises the one terminal and the other terminal always contacts the other contact member.

5. The medical device according to claim 1, wherein the terminals are positioned in a housing, the one contact member comprising a collar positioned in the housing, and a spring biased contact member mounted in the collar and exposed outside the collar to be contacted by the one terminal.

6. The medical device according to claim 1, wherein the sticking moving-member is a wire at least partially positioned in a housing and extending outside the housing, and the sandwiching moving-member is a wire at least partially positioned in the housing and extending outside the housing.

7. The medical device according to claim 6, further comprising a manually operable sticking moving-lever connected to the sticking moving-member so that manual operation of the sticking moving-lever results in movement of the wire constituting the sticking moving-member, and a manually operable sandwiching moving-lever connected to the sandwiching moving-member so that manual operation of the sandwiching moving-lever results in movement of the wire constituting the sandwiching moving-member, the sandwiching moving-lever and the sticking moving-lever being movable relative to the housing.

8. A medical device comprising:
a catheter configured to be positioned in a blood vessel;
a sticking member having a sharp distal end for sticking a biological tissue at a periphery of a defect existing in the biological tissue, the sticking member being movably positioned in the catheter;
a sandwiching member cooperating with the sticking member to sandwich the biological tissue between the sticking member and the sandwiching member to close the defect, the sandwiching member being movably positioned in the catheter;
an electric supply source for supplying electrical energy;
first and second contact members each electrically connected to the electric supply source;
a movable sticking moving-member connected to the sticking member so the sticking moving-member and the sticking member move together and movement applied to the sticking moving-member causes movement of the sticking member;
a movable sandwiching moving-member connected to the sandwiching member so the sandwiching moving-member and the sandwiching member move together and movement applied to the sandwiching moving-member causes movement of the sandwiching member;
a first terminal connected to the sticking moving-member so the first terminal and the sticking moving-member move together;
a second terminal connected to the sandwiching moving-member so the second terminal and the sandwiching moving-member move together, at least one of the first and second terminals not contacting a respective one of the first and second contact members in an initial state;
the sticking moving-member being movable to move the sticking member to a sticking state in which the sharp distal end of the sticking member can penetrate the biological tissue, and the sandwiching moving-member being movable to move the sandwiching member to a sandwiching state in which the sandwiching member cooperates with the sticking member in the sticking state to sandwich the biological tissue between the sticking member and the sandwiching member to close the defect; and
the first terminal moving from the initial state to contact the first contact and the second terminal contacting the second contact during the sandwiching state so that electrical energy from the electric energy supply is supplied to the sticking member and the sandwiching member only in the sandwiching state to fuse together the biological tissue sandwiched between the sandwiching member and the sticking member.

9. The medical device according to claim 8, wherein the first and second contact members are electrically connected to the electric supply source by respective wires, one of the wires including an on-off switch to on-off control electric current from the energy supply means to the first and second contact members.

10. The medical device according to claim 8, wherein the sticking moving-member is connected to a manually operable sticking moving-lever, and the sandwiching moving-member is connected to a manually operable sandwiching moving-lever, the manually operable sticking moving-lever and the manually operable sandwiching moving-lever each including a connector electrically connected to a respective electrical connection member of the electric supply source.

11. The medical device according to claim 8, wherein the first and second terminals are located in a housing, the first contact member comprising a first collar positioned in the housing, and a first contact mounted in the collar and urged in a direction outside the collar by a spring.

12. The medical device according to claim 8, wherein the sticking moving-member is a wire at least partially positioned in a housing and extending outside the housing, and the sandwiching moving-member is a wire at least partially positioned in the housing and extending outside the housing.

13. The medical device according to claim 12, wherein the first and second terminals are located in a housing, further comprising a slidable sticking moving-lever connected to the wire constituting the sticking moving-member so that sliding movement of the sticking moving-lever results in movement of the wire constituting the sticking moving-member, and a manually operable sandwiching moving-lever connected to the sandwiching moving-member so that manual operation of the sandwiching moving-lever results in movement of the wire constituting the sandwiching moving-member, the sandwiching moving-lever and the sticking moving-lever being movable relative to the housing.

14. A medical device comprising:
a catheter configured to be positioned in a blood vessel;
a sticking member movably positioned in the catheter and possessing a sharp distal end to penetrate a biological tissue at a periphery of a defect existing in the biological tissue, the sharp distal end of the sticking member configured to penetrate the biological tissue by entering the biological tissue from one side and exiting the biological tissue at an opposite side;
a housing positioned proximally of the catheter;
a manually operable sticking moving-lever movably mounted on the housing and connected to the sticking member by way of a sticking moving-member so that manual operation of the sticking moving-lever results in movement of the sticking member by way of the sticking moving-member to position the sticking member in a penetrating state in which the sticking member penetrates the biological tissue, the sticking moving-member extending from the housing to an interior of the catheter;

a movable operation rod possessing a distal end configured to contact the opposite side of the biological tissue to hold the opposite side of the biological tissue as the sticking member penetrates the biological tissue;

an operation lever movably mounted relative to the housing; and a lock mechanism mounted in the operation lever and through which the operation rod passes, the lock mechanism including a movable engaging member movable between an unlocked position in which the engaging member permits the operation rod to move relative to the operation lever to move the distal end of the operation rod into contact with the opposite side of the biological tissue to hold the opposite side of the biological tissue, and a locked position in which the engaging member holds the operation rod against movement relative to the operation lever to fix the distal end of the operation rod in position to hold the opposite side of the biological tissue as the sticking moving-lever is moved to the penetrating state in which the sticking member penetrates the biological tissue from the one side.

15. The medical device according to claim 14, further comprising a sandwiching member which cooperates with the sticking member in the penetrating state to sandwich the biological tissue between the sticking member and the sandwiching member to close the defect, the sandwiching member being connected to the operation lever by way of a tube fixed to the operation lever.

16. The medical device according to claim 15, further comprising a sleeve body movably positioned on the operation rod so that the operation rod passes through a through hole in the sleeve body, and a plurality of wires each having one end portion fixed to the sleeve body and an opposite end fixed to a distal end of the tube.

17. The medical device according to claim 16, wherein the sleeve body is a first sleeve body and further comprising a second sleeve body movably positioned on the operation rod so that the operation rod passes through a through hole in the second sleeve body, the first sleeve body being positioned between the second sleeve body and the distal end of the tube, and a plurality of wires each having one end portion fixed to the first sleeve body and an opposite end fixed to a bump member at a distal end of the operation rod.

18. The medical device according to claim 14, further comprising a sandwiching member cooperating with the sticking member in the penetrating state to sandwich the biological tissue between the sticking member and the sandwiching member to close the defect, the sandwiching member being movably positioned in the catheter.

19. The medical device according to claim 18, further comprising a movable sandwiching moving-member connected to the sandwiching member to move the sandwiching member, and a pair of terminals including a first terminal and a second terminal, the first terminal connected to the sandwiching moving-member so the first terminal moves together with the sandwiching moving-member, the second terminal being connected to the sticking moving-member so the second terminal moves together with the sticking moving-member; and a pair of spaced apart contact members connected to an electric supply source that supplies electrical energy to the contacts, the first terminal contacting one of the contact members during movement of the sandwiching moving-member, the second terminal contacting the other one of the contact members during movement of the sticking moving-member.

* * * * *